(12) United States Patent
Clark et al.

(10) Patent No.: US 12,138,357 B2
(45) Date of Patent: *Nov. 12, 2024

(54) ULTRAVIOLET DISINFECTION DEVICE AND METHOD

(71) Applicant: Humn, Inc., Chicago, IL (US)

(72) Inventors: Brian Clark, Chicago, IL (US);
Andrea Lee Clark, Chicago, IL (US);
Daniel Lawrence Clark, Hermosa Beach, CA (US)

(73) Assignee: Humn, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/617,229

(22) Filed: Mar. 26, 2024

(65) Prior Publication Data
US 2024/0252700 A1    Aug. 1, 2024

Related U.S. Application Data

(63) Continuation of application No. 18/045,686, filed on Oct. 11, 2022.
(Continued)

(51) Int. Cl.
*A61L 2/10* (2006.01)
*A61L 2/24* (2006.01)

(52) U.S. Cl.
CPC ............. *A61L 2/10* (2013.01); *A61L 2/24* (2013.01); *A61L 2202/11* (2013.01); *A61L 2202/122* (2013.01); *A61L 2202/14* (2013.01)

(58) Field of Classification Search
CPC .......... A61L 2/10; A61L 2/24; A61L 2202/11; A61L 2202/122; A61L 2202/14
See application file for complete search history.

(56) References Cited

U.S. PATENT DOCUMENTS 10,894,104 B1 * 1/2021 Kim ..................... A61L 9/20
10,898,601 B2 * 1/2021 Majdali ................. A61L 2/10
(Continued)

OTHER PUBLICATIONS

Kitagawa et al., "Effect of intermittent irradiation and fluence-response of 222 nm ultraviolet light on SARS-CoV-2 contamination", Photodiagnosis and Photodynamic Therapy 33 (2021) 102184, 4 pages.
(Continued)

*Primary Examiner* — Regina M Yoo
(74) *Attorney, Agent, or Firm* — Morgan, Lewis & Bockius LLP

(57) ABSTRACT

A far-ultraviolet (far-UVC) disinfection device including a light source positioned within a housing and configured to emit a far-UVC light having an output wavelength of between about 206 nanometers to about 230 nanometers. There are one or more subject detection sensors positioned configured to detect the presence of one or more subjects and a controller in communication with the light source and the one or more subject detection sensors. The controller is configured to receive detection data from the one or more subject detection sensors and determine whether one or more subjects are within a range of the far-UVC light emitted by the light source. The controller is further configured to cause the light source to emit or cease emitting far-UVC light based on the amount of time one or more subjects are within the range of the emitted. far-UVC light.

19 Claims, 18 Drawing Sheets

Related U.S. Application Data

(60) Provisional application No. 63/232,292, filed on Aug. 12, 2021.

(56) References Cited

U.S. PATENT DOCUMENTS

| | | | | |
|---|---|---|---|---|
| 11,184,739 | B1* | 11/2021 | Wellig | H04W 4/029 |
| 2018/0055959 | A1* | 3/2018 | Lin | A61L 2/10 |
| 2018/0064833 | A1* | 3/2018 | Childress | B64D 11/02 |
| 2020/0254122 | A1* | 8/2020 | Starkweather | A61L 2/10 |
| 2021/0113724 | A1* | 4/2021 | Ufkes | A61L 9/20 |
| 2021/0361810 | A1* | 11/2021 | Glanz | A61L 2/0005 |
| 2021/0369881 | A1* | 12/2021 | Hayden | A61L 2/0023 |
| 2022/0008581 | A1* | 1/2022 | Hawk | A63B 71/0036 |
| 2022/0016297 | A1* | 1/2022 | Huang | A61L 2/10 |
| 2022/0023468 | A1* | 1/2022 | Sears | B64D 11/00 |
| 2022/0072184 | A1* | 3/2022 | Groves | A61L 2/08 |
| 2022/0193280 | A1* | 6/2022 | James | A61L 9/20 |
| 2022/0202968 | A1* | 6/2022 | Shan | A61L 2/26 |
| 2023/0053659 | A1 | 2/2023 | Hood et al. | |
| 2023/0056649 | A1 | 2/2023 | Hood et al. | |

OTHER PUBLICATIONS

Welch et al., "Far-UVC light; A new tool to control the spread of airborn-mediated microbial diseases", Scientific Reports | (2018) 8:2752 | DOI: 10.1038/s41598-018-21058-w, 7 pages.

Shimoda et al., "Efficany of 265-nm ultraviolet light in inactivating infectious SARS-CoV-2" Journal of Photochemistry and Photobiology 7 (2021) 100050, 3 pages.

Eadie et al., "Far-UVC (222nm) effciently inactivates an airborne pathogen in a room-sized chamber", Scientific Reports (2022) 12:4373 | https://doi.org/10.1038/s41598-022-08462-z, 9 pages.

Christiane Silke Heilingloh PhD et al., "Susceptibility to SARS-CoV-2 to UV irradiation", American Journal of Infection Control 48 (2020) 1273-1275.

Renata Sest-Costa et al., "UV 254 nm is more efficient than UV 222 nm in inactivating SARS-CoV-2 present in human saliva", Photodiagnosis and Photodynamic Therapy 39 (2022) 103015, 8 pages.

Sabino et al., "UV-C (254 nm) lethal doses for SARS-CoV-2", Photodiagnosis and Photodynamic Therapy 32 (2020) 101995, 2 pages.

Hanamura et al., "Viability evaluation of layered cell sheets after ultraviolet light irradiation of 222 nm", Regenerative Therapy 14 (2020) 344-351.

Care222® Filtered Far UV-C Excimer Lamp Module, Filtered Krypton-Chloride 222nm Technology, www.ushio.com, available at least as early as Aug. 15, 2021, 4 pages.

Electroluminescent Lime Green Night Light (Two-Pack), https://www.exitsignwarehouse.com/products/, available as early as Mar. 15, 2023, 2 pages.

\* cited by examiner

ULTRAVIOLET DISINFECTION DEVICE AND METHOD

CROSS-REFERENCE TO RELATED APPLICATIONS

This application is a continuation of U.S. patent application Ser. No. 18/045,686 filed Oct. 11, 2022, which claims the benefit of U.S. Provisional Patent Application No. 63/232,292 filed Aug. 12, 2021 entitled "Light Systems That Clean and Disinfect Air", each of which is incorporated by reference herein in its entirety.

TECHNICAL FIELD

The present disclosure generally relates to light systems for disinfection and, in some embodiments, to an ultraviolet light disinfection device and method of use thereof.

SUMMARY

In one embodiment there is a far-UVC disinfection device including a housing, a light source positioned within the housing and configured to emit a far-UVC light having an output wavelength of between about 206 nanometers to about 230 nanometers, one or more subject detection sensors positioned within the housing and configured to detect the presence of one or more subjects, the one or more subjects consisting of one or more of human beings, one or more domesticated animals, and one or more farm animals or a combination thereof, and a controller positioned within the housing and in communication with the light source and the one or more subject detection sensors. The controller is configured to receive detection data from the one or more subject detection sensors, determine, based on the received detection data, whether one or more subjects are within a range of the far-UVC light emitted by the light source, in response to determining that a subject of the one or more subjects are within the range of the far-UVC light emitted by the light source for a predetermined amount of exposure time, cause the light source to cease emitting the far-UVC light, and in response to determining that no subject of the one or more subjects is within the range of the far-UVC light emitted by the light source for the predetermined amount of exposure time, cause the light source to emit the far-UVC light.

In some embodiments, the one or more subject detection sensors includes at least one of an infrared sensor, a motion sensor, and a proximity sensor. In some embodiments, the predetermined amount of exposure time is less than or equal to an exposure limit for the subject being exposed to the far-UVC light emitted by the light source. In some embodiments, the controller is configured to cause the light source to cease emitting the far-UVC light in response to the one or more subject detection sensors detecting the presence of a subject within the range of the emitted far-UVC light for between about one minute to about ten minutes. In some embodiments, the controller is configured to cause the light source to cease emitting the far-UVC light in response to the one or more subject detection sensors detecting the presence of a subject within the range of the emitted light for about six minutes.

In some embodiments, the controller is configured to determine an effective disinfection rate based on an amount of time that the light source has been emitting the far-UVC light. In some embodiments, the controller is configured to transmit the determined effective disinfection rate to a client device external to the far-UVC disinfection device. In some embodiments, the one or more subject detection sensors includes two infrared sensors and four motion sensors. In some embodiments, the controller is configured to cause the one or more subject detection sensors to activate at a predetermined detection interval, and when activated, the one or more subject detection sensors are configured to generate the detection data and transmit the detection data to the processor.

In some embodiments, the predetermined detection interval is less than or equal to one second. In some embodiments, the controller is configured to delay causing the light source to emit the far-UVC light in response to the one or more subject detection sensors detecting no subject within the range of the far-UVC light emitted by the light source by a predetermined amount of delay time. In some embodiments, the predetermined amount of delay time is between about one second to six minutes. In some embodiments, the controller is configured to, in response to the light source emitting the far-UVC light continuously for a predetermined maximum emission amount of time, causing the light source to cease emitting the far-UVC light. In some embodiments, the predetermined maximum emission amount of time is about sixty minutes.

In some embodiments, the light source is configured to emit a far-UVC light having an output wavelength of about 222 nanometers. In some embodiments, the controller is configured to cause the light source to cease emitting the far-UVC light in response to the one or more subject detection sensors detecting the presence of a subject within the range of the emitted far-UVC light for a threshold limit value (TLV) amount of time, wherein the TLV is based on the output wavelength of the emitted far-UVC light. In some embodiments, the controller is configured to cause the light source to cease emitting the far-UVC light in response to the one or more subject detection sensors detecting the presence of a subject within a predetermined distance of the light source 104. In some embodiments, the predetermined distance is about three feet.

In another embodiment, there is A method of automatically disinfecting the air and surfaces within the range of a far-ultraviolet (far-UVC) disinfection device, the method including causing a far-UVC disinfection device to emit a far-UVC light having an output wavelength of about 222 nanometers, the far-UVC disinfection device including a far-UVC light source configured to emit the far-UVC light, one or more subject detection sensors configured to detect the one or more subjects, the one or more subjects consisting of one or more of human beings, one or more domesticated animals, and one or more farm animals or a combination thereof, and a controller in communication with the far-UVC light source and the one or more subject detection sensors and configured to selectively activate and deactivate each of the far-UVC light source and the one or more subject detection sensors. The method further includes in response to the one or more subject detection sensors detecting that a subject of the one or more subjects are within the range of the far-UVC light emitted by the far-UVC light source for a predetermined amount of exposure time, transmitting a deactivation signal from the controller to the far-UVC light source to cause the far-UVC light source to cease emitting the far-UVC light, and in response to the one or more subject detection sensors detecting no subject of the one or more subjects within the range of the far-UVC light emitted by the far-UVC light source, transmitting an activation signal from the controller to the far-UVC light source to cause the far-UVC light source to begin emitting the far-UVC light.

In some embodiments, the method further includes receiving from a client device, external to the far-UVC disinfection device, at the controller, an indication of a desired continuous activation period for the far-UVC light source, the desired continuous activation period defined by a start time and a stop time, at the start time, transmitting from the controller to the far-UVC light source the activation signal causing the far-UVC light source to emit far-UVC light, at a first time following the start time and prior to the stop time, determining via the one or more subject detection sensors that a subject is within range of the far-UVC light emitted by the light source, and transmitting the deactivation signal from the controller to the far-UVC light source to cause the far-UVC light source to cease emitting the far-UVC light, at a second time following the first time and prior to the stop time, determining that no subject is within the range of the far-UVC light emitted by the far-UVC light source, and transmitting the activation signal from the controller to the far-UVC light source to cause the far-UVC light source to begin emitting the far-UVC light, and at the end time, transmitting from the controller to the far-UVC light source the deactivation signal causing the far-UVC light source to cease emitting the far-UVC light.

BRIEF DESCRIPTION OF THE DRAWINGS

The foregoing summary, as well as the following detailed description of embodiments of the ultraviolet disinfection device and method, will be better understood when read in conjunction with the appended drawings of exemplary embodiments. It should be understood, however, that the invention is not limited to the precise arrangements and instrumentalities shown.

In the drawings.

DETAILED DESCRIPTION

Figure 1:
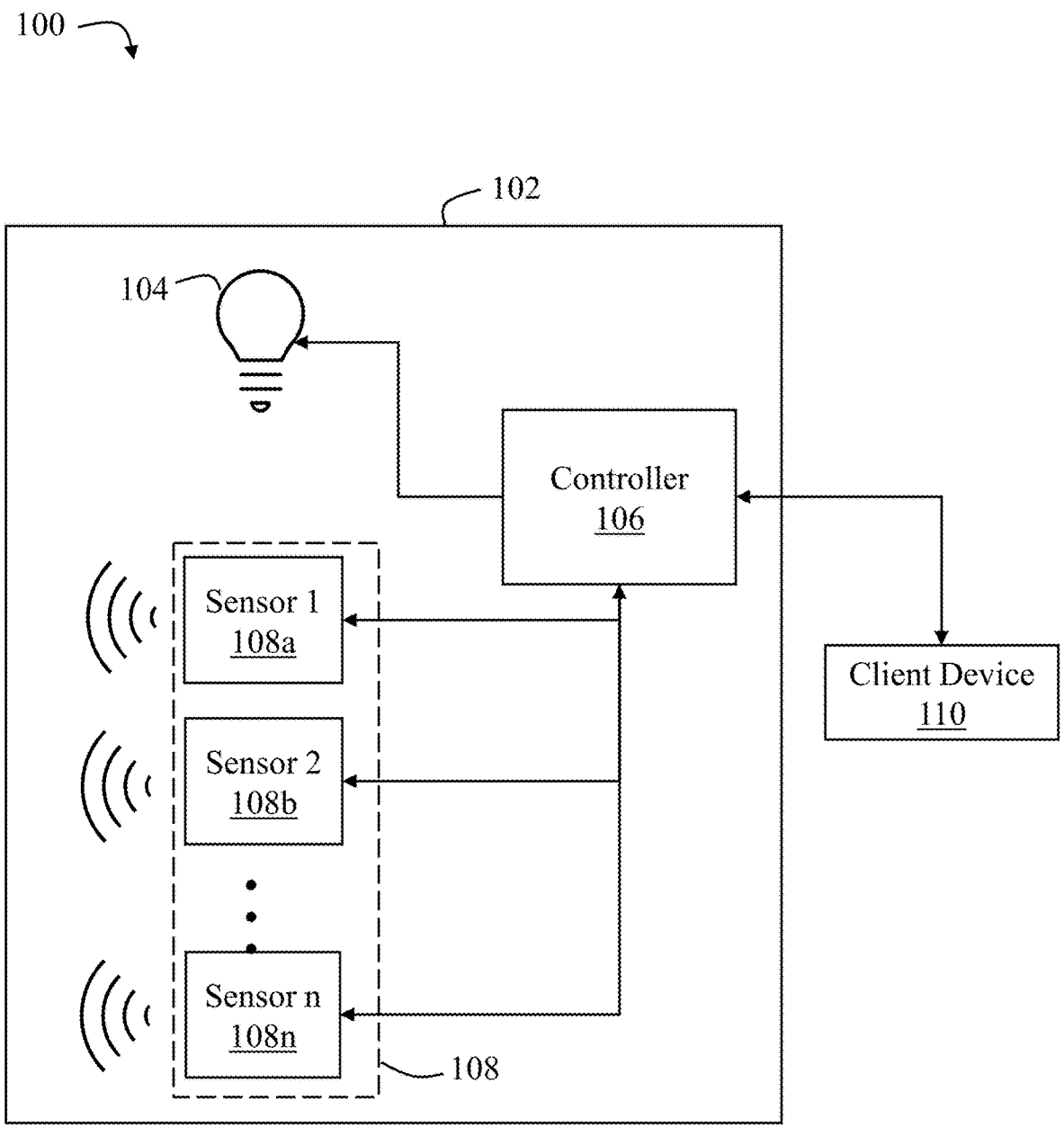
FIG. 1 is a block diagram of an ultraviolet disinfection device in accordance with an exemplary embodiment of the present invention.

Ultraviolet germicidal irradiation (UVGI) is one of many disinfection methods that use Ultraviolet (UV) light to kill or inactivate microorganisms by destroying nucleic acids and disrupting their DNA, leaving them unable to perform vital cellular function. However, existing and/or commercially available UVGI devices emit a UV light that is unsafe to subjects such as human beings and animals such as domesticated animals and farm animals. For example, the wavelength of the UV light emitted by such devices can cause permanent damage to subjects within a very short time frame (e.g., within a couple of seconds) of being exposed to said UV light. Put another way, the UV light emitted by such devices is nearly immediately harmful to the subjects outlined above.

Additionally, there is a need to effectively disinfect the air and various surfaces within a given indoor or outdoor public or private space. For example, it is difficult to effectively kill or inactivate airborne viruses and/or bacteria that exist within homes and other public or private spaces. As such, there is a need to provide an ultraviolet disinfection device, which emits a UV light to disinfect the air and surfaces within a public or private space, and which is safe to operate around subjects such as human beings, domesticated animals (e.g., household pets) and/or farm animals.

Numerous details are described herein in order to provide a thorough understanding of the example embodiment illustrated in the accompanying drawings. However, some embodiments may be practiced without any of the specific details, and the scope of the claims is only limited by those features and aspects specifically recited in the claims. Furthermore, well-known methods, components, and circuits have not been described in exhaustive detail so as not to unnecessarily obscure pertinent aspects of the embodiments described herein.

Aspects of the present invention are described with reference to the safety of an emitted UV light in relation to subjects (e.g., human being, domesticated animal, farm animal) exposed to the UV light. The "safety" of the UV light may refer to an amount of time needed to cause damage to the subject in response to the subject being exposed to the UV light. Damage to a subject from an emitted UV light may include, but is not limited to, skin damage (e.g., sunburn), damage to the subjects DNA, inflammation of the subjects cornea, temporary or permanent vision impairment, blindness, DNA lesions, erythema, and/or photo-keratitis. In some embodiments, the amount of time needed to cause damage to the subject may refer to the threshold limit value (TLV) for UV exposure. The TLV for UV exposure may be dictated by one or more existing trade organizations or standards organizations such as, but not limited to, the American Conference of Governmental Industrial Hygienists (ACGIH) or Illuminating Engineering Society (IES). The TLV may be calculated based on the output wavelength of the UV light, distance of a subject from the origin point of the UV light (e.g., a light source), an amount of time a subject is exposed to the UV light, the frequency at which a subject is exposed to the UV light, and/or the strength of the UV light (e.g., amount of radiation released by the UV light). according to means known to those skilled in the art. The TLV may represent the maximum allowable time a subject may be continuously exposed to a UV light before adverse effects or damage is caused to the subject. In some embodiments, a UV light having an associated TLV of greater than or equal to about 23 mJ/cm$^2$ may be considered safe whereas a UV light having an associated TLV of less than 23 mJ/cm$^2$ may be considered unsafe. In some embodiments, a UV light may be considered "safe" for purposes of this disclosure, if the UV light does not cause adverse effects and/or damage to a subject after being continuously exposed to the UV light for about at least six minutes, ten minutes, twelve minutes, or fifteen minutes.

A subject, as referenced herein may be a group consisting of one or more of human beings, one or more domesticated animals, and/or one or more farm animals. For example a human infant, child, adolescent and/or adult would be considered a subject for purposes of this disclosure whereas a fly may not. Further to this example, domesticated animals may refer to any animal commonly kept as a pet in family households in the United States, including, but not limited to dogs, cats, guinea pigs, rabbits and hamsters; and any animals commonly kept for companion or commercial purposes. It should be understood that domesticated animals may include amphibians, reptiles, and certain insects that human beings may keep as pets. A farm animal may refer to an animal farmed commercially for its meat, its skin or anything else produced by it (e.g., cows, pigs, sheep).

Figure 2:
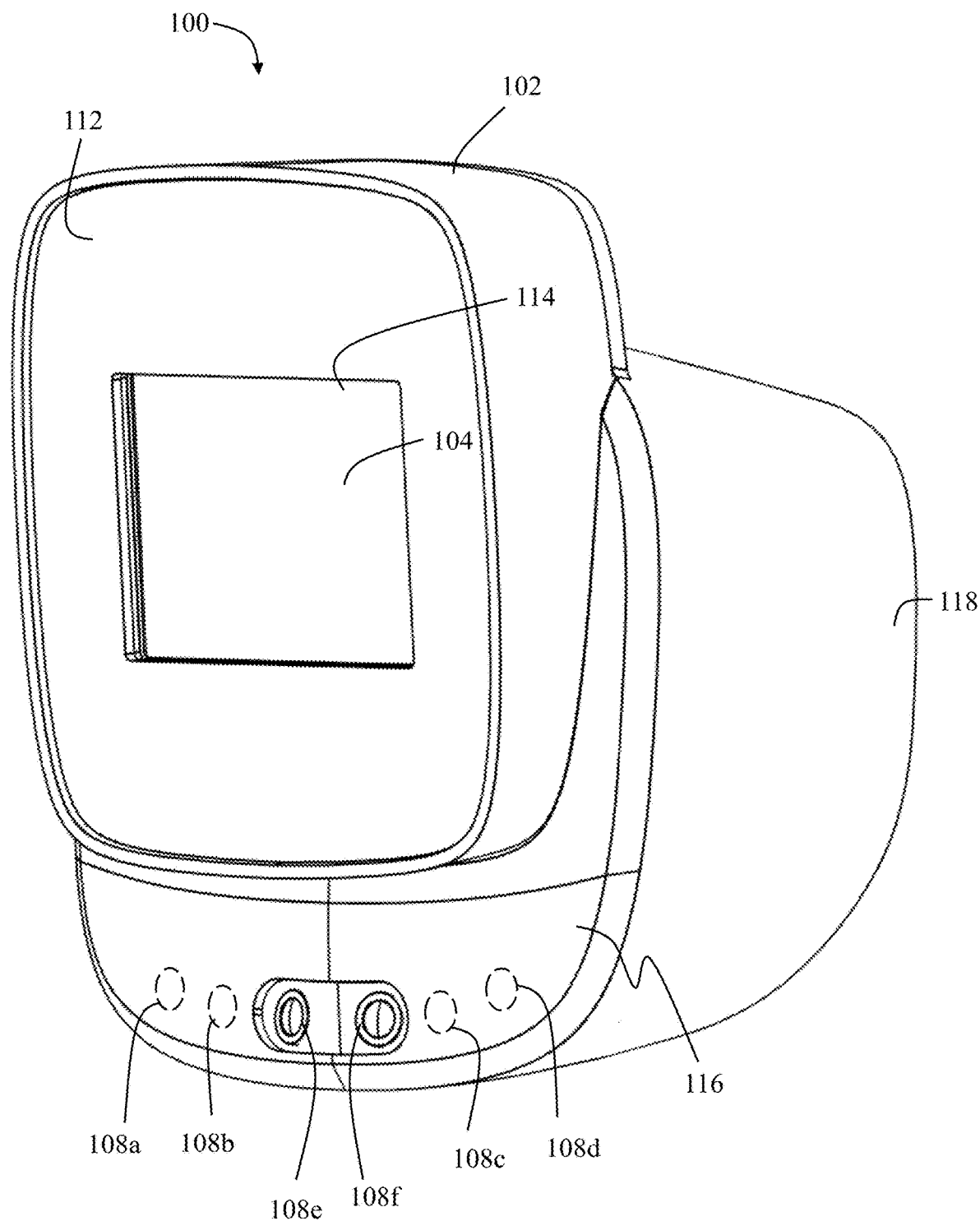
FIG. 2 is perspective view of the ultraviolet disinfection device of FIG. 1.

Referring to the drawings in detail, wherein like reference numerals indicate like elements throughout, there is shown in FIGS. 1-2 an ultraviolet disinfection device, generally designated 100, in accordance with an exemplary embodiment of the present invention. The UV device 100 may be configured to be positioned within a public or private space and safely emit a UV light that disinfects the air and/or surfaces within the emission range of the UV light.

Referring to FIGS. 1-2, the UV device 100 may include a housing 102, a light source 104, a controller 106, and one or more subject detection sensors 108. The light source 104, a controller 106 including one or more processors, and/or subject detection sensors 108 may be coupled to the housing 102. In some embodiments, the light source 104, controller 106, and/or the subject detection sensors 108 are positioned within the housing 102. The controller 106 may be in communication with the light source 104 such that the controller 106 may selectively activate and deactivate the light source 104. The controller 106 may also be in communication with the one or more subject detection sensors 108 such that the controller 106 may determine whether a subject is within the range of the UV light emitted by the light source 104. In some embodiments, the UV device 100 may include one or more light sources 104 each in communication with the controller 106. For sake of brevity, the UV device 100 will be described with reference to a single light source 104. In some embodiments, the UV device 100 may be a far-UVC disinfection device 100 configured to emit a far-UVC light (e.g., the light source 104 may be a far-UVC light source configured to emit a far-UVC light).

The controller 106 may include one or more processors and/or one or more memory units configured to store and execute executable code for controlling operations of the UV device 100 discussed herein. For example, the controller 106 may be in communication with the one or more subject detection sensors 108 and/or the light source 104 to control operation thereof. In some embodiments, the controller 106 includes a substrate (e.g., a printed circuit board (PCB)) having electrically connected thereto one or more memory devices (e.g., read-only memory (ROM), flash memory, dynamic random-access memory (DRAM), or static memory), and a processing unit (e.g., a processor, a microprocessor, an application specific integrated circuit (ASIC), or the like).

In some embodiments, the UV device 100 may include a power source (not shown) electrically connected to the light source 104, the controller 106, the one or more subject detection sensors 108 and/or any other electrically powered components coupled to the housing 102. The power source may be a battery pack configured to receive one or more batteries. In other embodiments, the power source may be a rechargeable power source. In other embodiments, the power source is electrically connected to a power cable to enable a user to plug the cable into an outlet connected to an electrical grid in the user's home.

In some embodiments, the UV device 100 may be in communication with one or more client devices 110 external to the UV device 100. For example, the controller 106 may include a network interface device to allow the controller to be in communication with a client device 110 over a local area network (LAN), wireless area network (WAN), Bluetooth, or any other communication means. The client devices 110 may be any computing device such as, but not limited to, a smart phone, a tablet computer, a laptop computer, and a desktop computer.

In one embodiment, the UV device 100 includes one or more computing devices (e.g., controller 106) having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

The light source 104 may be configured to emit a UV light to clean and/or effect disinfection of the air and/or surfaces within the emission range of the emitted UV light. In some embodiments, when the UV device 100 includes more than one light source 104 for emitting UV light, the light sources 104 may output UV light at different intensities. In some embodiments, the light source 104 may be considered a UV germicidal irradiation (UVGI) light source. For example, the light source 104 may emit a UV light to kill or inactivate microorganisms within the air and/or present on surfaces within the range of the emitted UV light. In some embodiments, the light source emits a far-UVC light. In some embodiments, the light source 104 is configured to emit a UV light having an output wavelength of between about 200 nanometers to about 254 nanometers. In some embodiments, the light source 104 is configured to emit a UV light having an output wavelength of between about 206 nanometers to about 230 nanometers. In some embodiments, the light source 104 is configured to emit a UV light having an output wavelength of about 222 nanometers. As such, the UV light emitted by the light source 104 may be safe for a subject to be exposed to (e.g., within the emission range of the emitted UV light) for an extended period of time.

An extended period of time may be relative to conventional UVGI devices. For example, conventional UVGI devices emit a UV light having a significantly lower TLV value than the light source 104 of the present disclosure. Further to this example, conventional UVGI devices have a TLV value typically between 3 mJ/cm$^2$ to about 6 mJ/cm$^2$ whereas the light source 104 of the present disclosure may have a TLV value of about 23 mJ/cm$^2$. As such a subject may be exposed to the light emitted by the light source 104 for a period of time that is between about two to about eight times longer than the UV light emitted by a conventional UVGI device. In this manner, the light source 104 may be actively emitting UV light for an amount of time to effect disinfection of the air and/or surfaces while a subject (e.g., human being, domesticated animal, farm animal) is simultaneously exposed to the UV light and before causing any adverse effects or damage to the subject (e.g., before the subject is exposed for a predetermined amount of exposure time).

There may be a maximum amount of time the subject may be exposed to the UV light, after which the subject may experience adverse effects or damage caused by the UV light. The maximum amount of time a subject may be exposed to the UV light before any adverse effects or damage is caused may generally be referred to herein as a subject exposure limit, or exposure limit for short. In some embodiments, the exposure limit is based on one or more regulations established by governing bodies, such as, but not limited to the Occupational Safety and Health Administration (OSHA), ACGIH, IES, and/or American National Standards Institute (ANSI). In some embodiments, an exposure limit is based on a one day, or 24-hour, cycle of exposure. As such, the UV device 100 may be configured to cease emitting the UV light prior to a subject being exposed to the UV light for the subject exposure limit amount of time. The one or more subject detection sensors 108 may be configured to detect and monitor the presence of subjects within at least the emission range of the UV light emitted by the light source 104. In some embodiments, the UV device 100 includes a plurality of subject detection sensors 108 each in communication with the controller 106. There may be one, two, three, four, five, six, seven, eight, nine, ten or more than ten subject detection sensors 108a-108n in communication with the controller 106. In some embodiments, the one or more subject detection sensors 108 includes at least one of an infrared sensor and a motion sensor. For example, and as illustrated in FIG. 2, the one or more subject detection sensors 108 may include four motion sensors 108a-108d and two infrared sensors 108e-108f. In some embodiments, the one or more subject detection sensors 108 may include a proximity sensor. For example, one or more of sensors 108a-108d may be a proximity sensor. In some embodiments, the subject detection sensors 108 may include a combination of infrared sensors, motion sensors, and/or proximity sensors.

In some embodiments, the one or more subject detection sensors 108 may be oriented such that a detection range of the one or more subject detection sensors 108 overlaps with the emission range of the light source 104. For example, and as illustrated in FIG. 2, the light source 104 may emit UV light through a front panel 112 of the housing 102. The front panel 112 may include a window 114 through which the light source 104 may emit the UV light. The window 114 may be comprised of a transparent or translucent material such that the UV light emitted by the 104 may pass therethrough. In some embodiments, the window 114 may act as a bandpass filter. In some embodiments, there may be one or more other light sources (e.g., LED lights) positioned behind the window and configured to activate and deactivate in conjunction with the light source 104. For example, when the light source 104 is activated and emitting UV light, the other light sources may also be activated such that a light visible to subjects can be seen through the window 114. In this manner, the UV device 100 may provide a visual indication to subjects (e.g., human beings) that light source 104 is actively emitting UV light.

The one or more subject detection sensors 108 may be coupled to the housing 102 and oriented such that detection signals emitted by the subject detection sensors 108 are generally in the same direction as the emitted UV light. In this manner, the one or more subject detection sensors 108 may be able to detect the presence of subjects, via the emitted detection signals, that are within the emission range of the emitted UV light. In some embodiments, the subject detection sensors are positioned below the light source 104 and oriented generally toward the front of the housing 102. For example, the housing 102 may include a sensor panel 116 that the one or more subject detection sensors 108 are coupled to. In some embodiments, at least a portion of one or more of the subject detection sensors 108 may be exposed at an exterior surface of the sensor panel 116. For example, the subject detection sensors 108e and 108f are shown as extending partially through the sensor panel 116. One or more other subject detection sensors 108 may be entirely enclosed within the housing 102 (e.g., not exposed at an exterior surface of the sensor panel 116). For example, subject detection sensors 108a-108d are entirely enclosed within the housing 102 and positioned behind the sensor panel 116. As such, the sensor panel 116 may be comprised of a material configured to permit detection signals emitted by one or more of the subject detection sensors 108 to pass therethrough. In this manner, the sensor panel 116 may obscure one or more of the subject detection sensors 108 from the sight of a subject, while not impeding the operation of the subject detection sensors 108. In some embodiments, the housing 102 may include a base 118 configured to mount the UV device 100 to a surface within a public or private space. For example, the base 118 may include mounting hardware (e.g., mounting brackets, screw holes, adhesives) to enable a user to mount the UV device 100 to a wall, ceiling, or any other desired surface within the user's home. In some embodiments, the base 118 is configured to be mounted to and/or removed from an external bracket to enable a user to easily couple and decouple the housing 102 to the external bracket. In some embodiments, the base 118 may be configured to allow a user to adjust the orientation and/or position of the housing 102 when the base 118 is connected to a surface. In some embodiments, the UV device 100 may be portable and the mounting base 118 may be configured to be placed on a generally flat surface (e.g., floor, table top, a shelf).

As such, the one or more subject detection sensors 108 may emit detection signals to detect and/or monitor the presence of and/or position of one or more subjects. The subject detection sensors 108 may generate detection data based on the emitted detection signals and transmit the detection data to the controller 106. In this manner, the controller 106 may, based on the received detection data, determine whether a subject is within range of the UV light emitted by the light source 104 and/or an amount of time a subject has been within range of the UV light. In some embodiments, the controller 106 is configured to selectively activate and/or deactivate the light source 104 based on the position of the subject relative to the UV light emission range, the time the subject has spent within the emission range of the UV light, and/or the proximity of the subject relative to the UV device 100. Put another way, the controller 106 may be configured to automatically cause the light source 104 to emit or cease emitting UV light based on 1) the location of one or more subjects relative to the UV device 100 and/or 2) an amount of time a subject has been exposed to the emitted UV light.

In some embodiments, the controller 106 is configured to selectively activate and/or deactivate the one or more subject detection sensors 108. For example, the controller 106 may transmit a sensor activation signal to the one or more subject detection sensors 108, individually or in combination, to cause the one or more subject detection sensors 108 to activate and thereby emit subject detection signals. In some embodiments, the controller 106 is configured to activate the subject detection sensors 108 at a predetermined detection interval. For example, the controller 106 may transmit a sensor activation signal to the one or more subject detection sensors 108 at a predetermined detection interval of, but not limited to, less than one second, one second, two seconds, five seconds, ten seconds, thirty seconds, or one minute.

In some embodiments, the UV device 100 is configured to automatically cease emitting UV light in response to a subject entering within a predetermined distance of the UV device 100. For example, the one or more subject detection sensors 108 may transmit detection data to the controller 106. Based on the detection data, the controller 106 may determine that a subject is within the range of the emitted UV light and is within the predetermined distance from the UV device 100. In response to determining that the subject is within the UV light range and the predetermined distance, the controller 106 may transmit a deactivation signal to the light source 104 to cause the light source 104 to cease emitting UV light. In some embodiments, the predetermined distance is a distance at which the UV light emitted by the light source 104 may cause adverse effects to or damage the subject. In some embodiments, the predetermined distance is about three feet. In some embodiments, one or more proximity sensors included in the subject detection sensors 108 may be used to determine whether a subject is within the predetermined distance.

In some embodiments, the UV device 100 is configured to distinguish between different subjects. For example, the UV device 100 may be configured to distinguish between a first subject and a second subject such that the UV device 100 may actively monitor the amount of time each subject has been exposed to UV light emitted by the light source 104. In some embodiments, the controller 106 is configured to distinguish between different subjects via the detection data generated by the subject detection sensors 108. For example, the detection data may include for each detected subject temperature profile data, and/or physical characteristic data (e.g., height, hair color, skin color, facial features). In this manner, the controller 106 may be configured to distinguish between different subjects. In some embodiments, there is a storage device (e.g., non-volatile memory, NAND die) operatively coupled to the controller 106 and configured to store detection data. As such, the controller 106 may associate a particular subject with subject specific detection data and transmit it to the storage device for storage and later retrieval.

In some embodiments, the one or more sensors 108 includes an image capture device (e.g., camera, video recorder) to enable the controller 106 to distinguish between different subjects. As such, the image capture device may transmit to the controller 106 detection data including images of one or more subjects. The controller 106 may be configured to perform image recognition on the received detection data to determine physical characteristics of the one or more subjects and generate physical characteristic data for each subject. For example, the controller 106 may be configured to perform an optical recognition (e.g., facial recognition) based on the images included in the detection data to distinguish between different subjects. In some embodiments, the UV device 100 is configured to anonymize subjects whom facial recognition has been performed on to ensure that the subjects identity is kept secret. In some embodiments, the controller 106 is configured to leverage artificial intelligence (AI) and/or machine learning in order to distinguish between different subjects. In some embodiments, the controller 106 may be configured to distinguish between different subjects based on the subjects, height, weight, location, gait, and/or any other physical attributes.

Referring to FIGS. 3A-7D, there are shown various use case diagrams illustrating one or more subjects interaction with the UV device 100. The use case diagrams shown in FIGS. 3A-7D are intended to better illustrate aspects of the present disclosure, specifically in relation to the automatic activation and deactivation of the light source 104 by the controller 106 in response to detection data received from the one or more subject detection sensors 108. As discussed above, the controller 106 may include one or more processors configured to implement the functionality of the UV device described herein. For example, the controller 106 may have stored in a non-transitory computer readable storage medium, computer readable executable code that when executed by the processor implements the functionalities described herein.

In FIGS. 3A-7D, the emission range 105 of the UV light emitted by the light source 104 and the detection range 107 of the one or more subject detection sensors 108 are illustrated as broken lines. It will be understood though that the emission range 105 and detection range 107 shown are for purposes of illustrating concepts of the present disclosure and are not intended to limit the emission range 105 of the light source 104 and the detection range 107 of the subject detection sensors 108. For example, in some embodiments, the emission range 105 and detection range 107 may be generally equal such that each overlaps with one another. In some embodiments, the detection range 107 of the subject detection sensors 108 is greater than the emission range 105 of the light source 104, as illustrated in FIGS. 3A-7D. In FIGS. 3A-7D, the UV device 100 is mounted to a wall within a public or private space (e.g., a wall in a user's home).

Figure 3A:
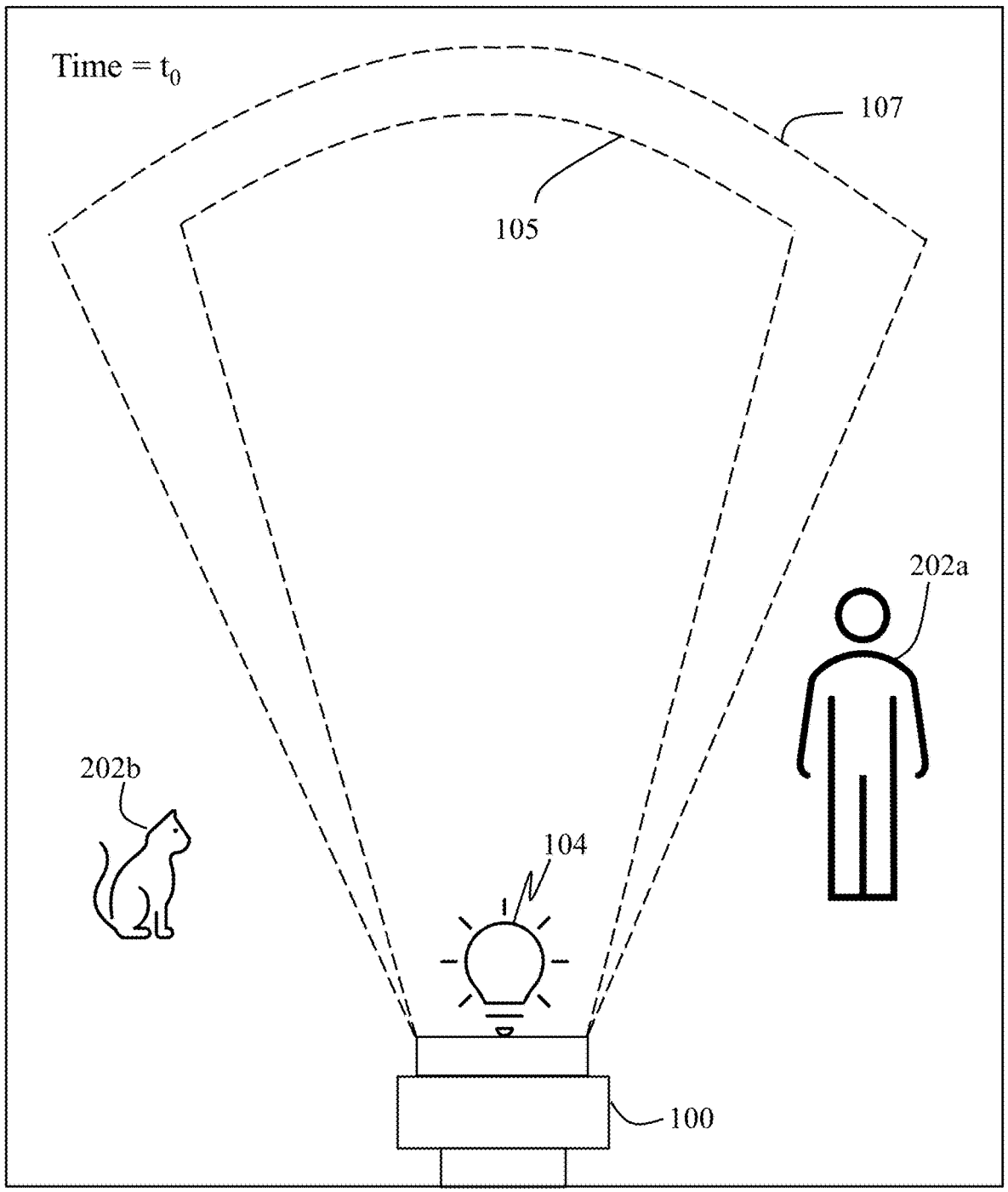
FIGS. 3A-3C are use case diagrams illustrating aspects of the present disclosure.
Figure 3B:
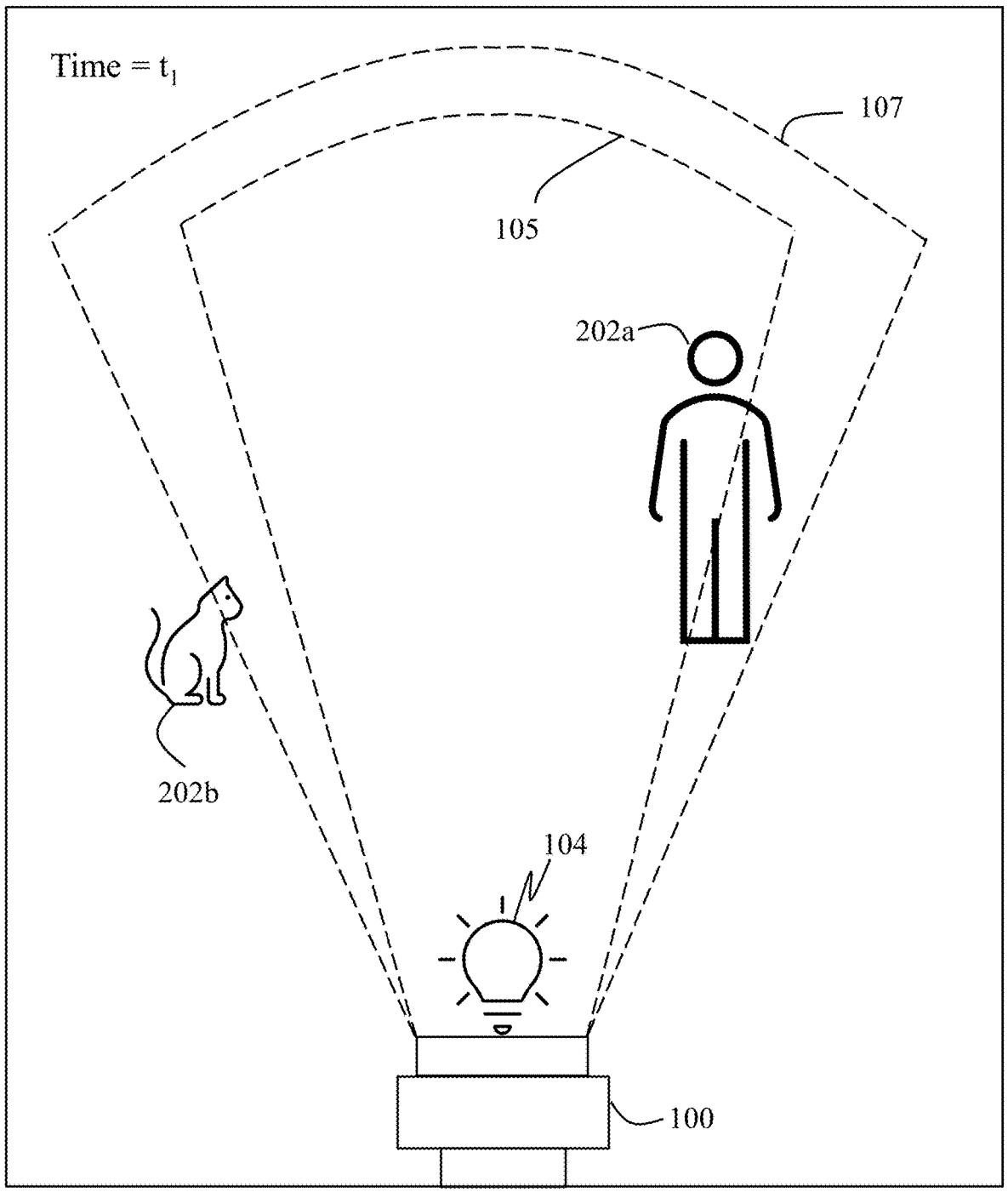
Figure 3C:
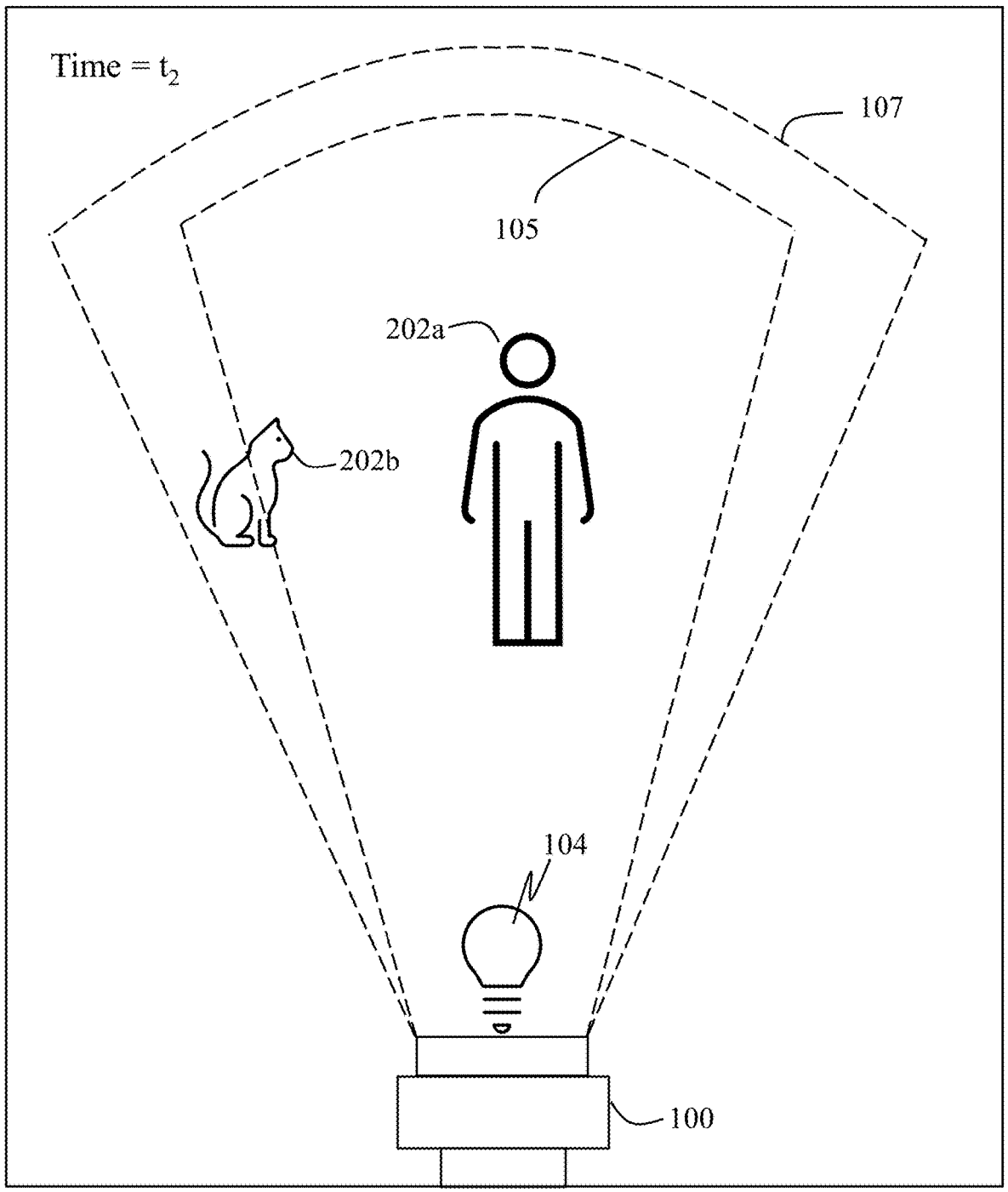

Referring to FIGS. 3A-3C, there is illustrated a first use case of one or more subjects 202a-202b interacting with the UV device 100. In FIG. 3A, neither of the subjects 202a-202b is within the emission range 105 of the light source 104 or the detection range 107 of the subject detection sensors 108 at time $t_0$. At time $t_0$, the controller 106 may receive detection data from the one or more subject detection sensors 108. The controller 106, may determine, based on the received detection data, that no subject is within the emission range 105 of the UV light emitted by the light source 104. In response to determining that no subject is within the emission range 105, the controller 106 may cause the light source 104 to emit the UV light.

In FIG. 3B, at a time $t_1$ occurring after the time $t_0$, the first subject 202a has moved within the emission range 105 and the second subject 202b has moved within the detection range 107. The controller 106 may be configured to determine, based on the detection data received from the subject detection sensors, that a subject is within range of the UV light emitted by the light source 104. For example, at time $t_1$ the subject detection sensors 108 may transmit detection data to the controller 106. The controller 106 may determine, based on the received detection data, that the first subject 202a is within the emission range 105 and that the second subject 202b is not. In FIG. 3B, time $t_1$ corresponds to the point in time at which the first subject 202a has moved from outside the emission range 105 to inside the emission range 105. The controller 106 may be configured to determine, based on the detection data, the amount of time a subject has been exposed to the emitted UV light. For example, the controller 106 may determine at time $t_1$ that the first subject 202a has been exposed to the emitted UV light for about one second and that the second subject 202b has not been exposed to the emitted UV light.

In some embodiments, the controller 106 is configured to cause the light source 104 to cease emitting the UV light based on the determined amount of time. For example, the controller 106 may be configured to determine if a subject has been within the emission range 105 for a predetermined amount of exposure time and if so, cause the light source 104 to cease emitting the UV light. The predetermined amount of exposure time may correspond to the subject exposure limit amount of time. In some embodiments, the predetermined amount of exposure time may be less than or equal to the exposure limit for a subject being exposed to the UV light emitted by the light source 104. In this manner, the controller 106 may cause the light source 104 to cease emitting the UV light prior to a subject being exposed thereto for the exposure limit amount of time. For example, if the subject exposure limit is fifteen minutes, then the predetermined amount of exposure time may be less than or equal to fifteen minutes. In some embodiments, the predetermined amount of exposure time is between about 20% to about 80% of the subject exposure limit amount of time. For example, if the subject exposure limit amount of time is fifteen minutes, the predetermined amount of exposure time may be six minutes.

The controller 106, in response to determining that the first subject 202a has not been exposed to the emitted UV light for a predetermined amount of exposure time, may cause the light source 104 to continue emitting the UV light. For example, the light source 104 was activated in FIG. 3A at time $t_0$ and at time $t_1$ the controller 106 determines that the first subject 202a has not been exposed to the UV light for the predetermined amount of exposure time. As such, the controller 106 may not transmit a deactivation signal to the light source 104, thereby causing the light source 104 to continue emitting UV light.

In FIG. 3C, at a time $t_2$ occurring after the time $t_1$ the first subject 202a has remained within the emission range 105 and the second subject has moved within the emission range 105. In some embodiments, the controller 106 is configured to, in response to determining that a subject is within the emission range 105 for the predetermined amount of exposure time, cause the light source 104 to cease emitting the UV light. The controller 106 may receive, between times $t_1$ and $t_2$ detection data from the subject detection sensors 108. For example, the controller 106 may cause the subject detection sensors 108 to emit a detection signal at a predetermined detection interval (e.g., every second) between times $t_1$ and $t_2$. Each time the subject detection sensors 108 are activated, detection data may be generated by the subject detection sensors 108 and transmitted to the controller 106.

The controller 106 may determine, based on the received detection data over a period of time (e.g., the period of time between times $t_1$ and $t_2$) the amount of time a subject has been within the emission range 105. For example, the controller 106 may determine that there has been a subject (e.g., first subject 202a, second subject 202b) within the emission range 105 for the period of time between times $t_1$ and $t_2$ based on the detection data received between those times. In response to the amount of time a subject has been within the emission range being greater than or equal to the predetermined amount of exposure time, the controller 106 may cause the light source 104 to cease emitting the UV light. For example, in FIG. 3C, the first subject 202a has been within the emission range 105 for an amount of time equal to $t_2-t_1$. The amount of time $t_2-t_1$ determined by the controller 106 may be equal to the predetermined amount of exposure time (e.g., six minutes), and as such, the controller 106 may transmit a deactivation signal to the light source 104 to cause the light source 104 to cease emitting UV light. In some embodiments, the controller 106 is configured to cause the light source 104 to cease emitting UV light in response to the one or more subject detection sensors 108 detecting the presence of a subject within the range of the emitted UV light for between about one minute to about ten minutes. Put another way, the predetermined amount of exposure time may be between about one minute to about ten minutes.

In some embodiments, the UV device 100 is configured to cause the light source 104 to cease emitting UV light in response to a subject moving within a predetermined distance of the UV device 100. For example, and referring back to FIG. 3B, if the first subject 202a had moved within a predetermined distance of the light source 104 at time $t_1$ and was within the emission range 105, the controller 106 may cause the light source 104 to cease emitting UV light at time $t_1$. In some embodiments, the controller 106 is configured to cease emitting UV light at the time that the subject detection sensors 108 determine that a subject is within the predetermined distance from the light source 104 regardless of the amount of time the subject has been exposed to, or not exposed to the emitted UV light. For example, at time $t_1$ the first subject 202a was first detected as being within the emission range 105. Regardless of an amount of time the first subject 202a had been exposed to the emitted UV light, the controller 106 may, in response to receiving detection data from the subject detection sensors 108 (e.g., one or more proximity sensors), determine that the first subject 202a is within the predetermined distance from the light source 104 and transmit a deactivation signal to the light source 104. In some embodiments, the predetermined distance is between about one foot to about eight feet. In some embodiments, the predetermined distance is about three feet. In some embodiments, if a subject is outside of the predetermined distance, the controller 106 may control operation of the light source 104 based on the predetermined amount of exposure time as discussed above.

In some embodiments, the controller 106 is configured to determine an amount of time that a particular subject of one or more subjects has been exposed to the UV light emitted by the light source 104. Referring to FIGS. 4A-4D, there is shown a second use case in which the controller 106 is configured to distinguish between different subjects and determine an amount of exposure time for each subject. As discussed above, the controller 106 may be configured to distinguish between different subjects based on the detection data generated by the one or more subject detection sensors 108. For example, in FIG. 4A, a first subject 202a is located within the emission range 105 and a second subject 202b is located outside the emission range 105 but within the detection range 107. At time $t_0$ the subject detection sensors 108 may transmit detection data to the controller 106 and the controller 106 may determine that there is a first subject 202a within the emission range 105 of the light source 104 and that there is a second subject 202b outside the emission range 105. Put another way, based on the received detection data at time $t_0$ the controller 106 may distinguish between the first and second subject 202a-202b.

The controller 106 may determine, based on the detection data received at time $t_0$ that the first subject 202a has not been within the emission range 105 for a period of time greater than or equal to the predetermined amount of exposure time (e.g., six minutes). As such, the controller 106 may cause, or may have previously caused, the light source 104 to emit UV light. As such, in FIG. 4A the light source 104 is actively emitting UV light to effect disinfection within the emission range 105 while the first subject 202a is within the emission range 105.

Figure 4A:
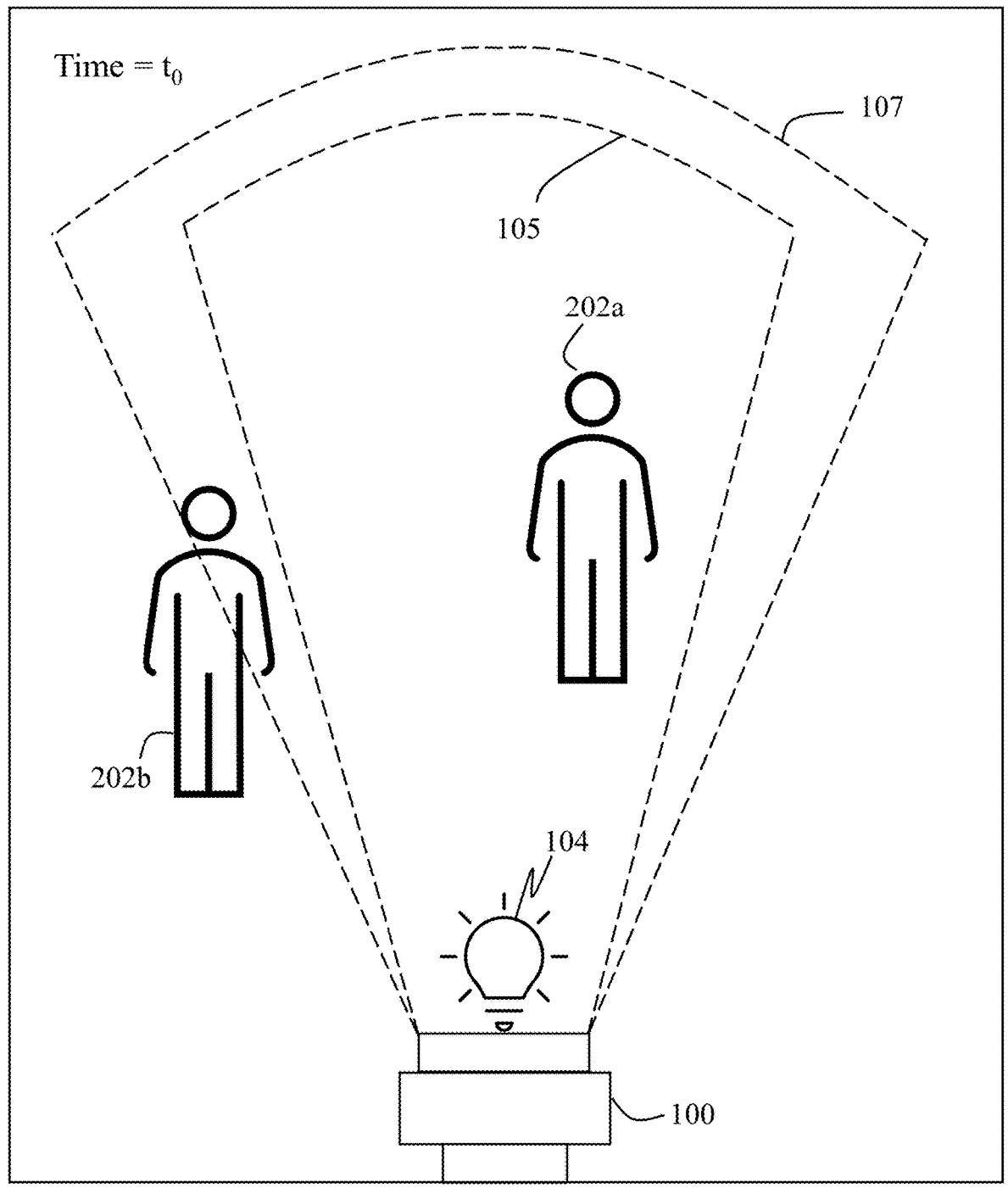
FIGS. 4A-4D are use case diagrams illustrating aspects of the present disclosure.
Figure 4B:
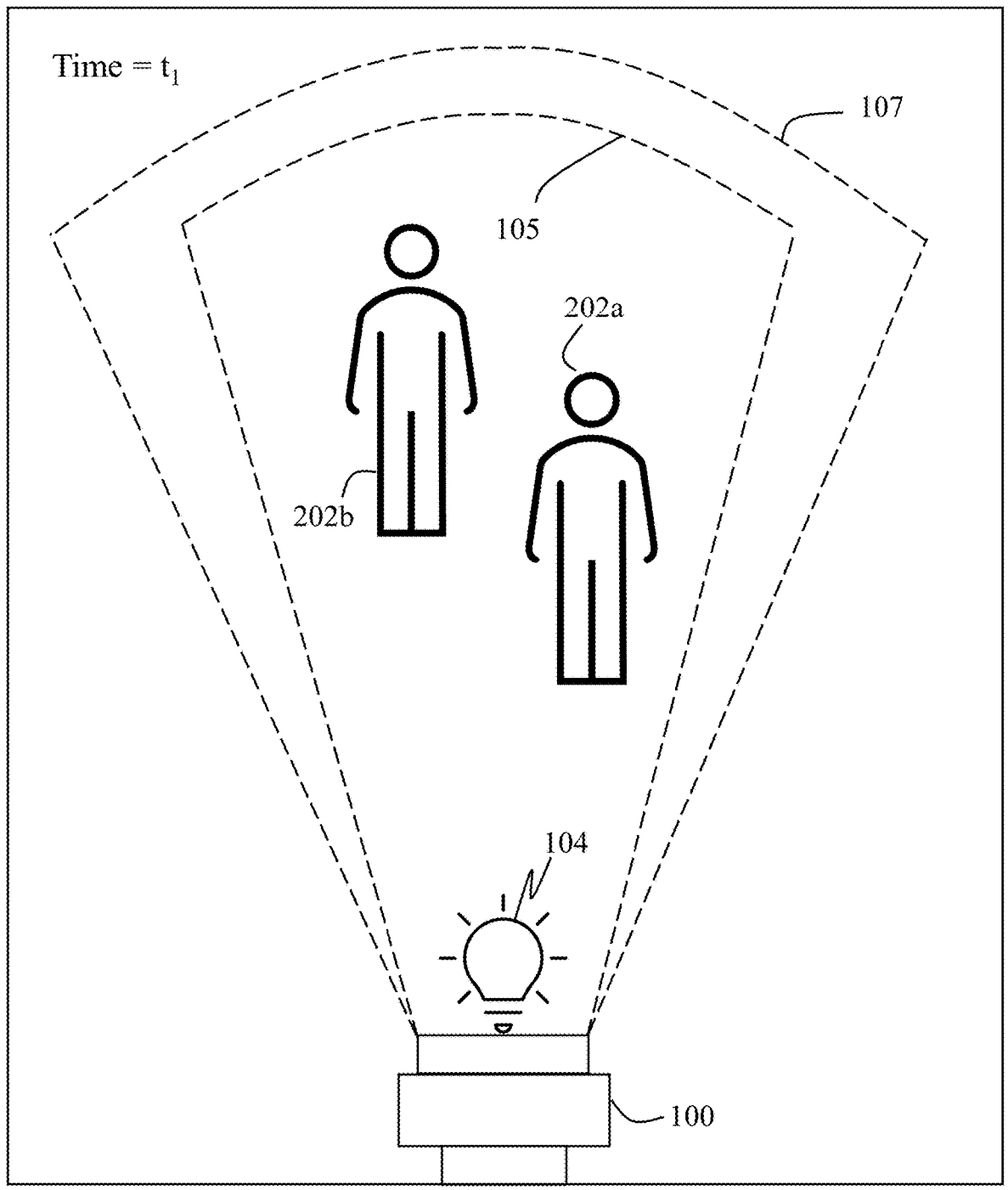

In FIG. 4B, at time $t_1$ occurring after time $t_0$ the second subject 202b is located within the emission range 105 simultaneously with the first subject 202a. At time $t_1$ the subject detection sensors may generate and transmit detection data to the controller 106. Furthermore, in the period of time between time $t_1$ and time $t_0$ the subject detection sensors 108 may have generated and transmitted detection data to the controller 106. The controller 106 may be configured to determine, based on the received detection data between times $t_1$ and $t_0$, the amount of time the first subject 202a and the amount of time the second subject 202b have been within the emission range 105. For example, if the amount of time between $t_1$ and $t_0$ is three minutes then the controller 106 may determine, based on the received detection data, that the first subject 202a has been within the emission range 105 for three minutes and that the second subject 202b has been within the emission range for less than one second (e.g., the second subject 202b moved within the emission range 105 at time $t_1$). In this manner, the controller 106 may be configured to determine the amount of exposure time for each of the first subject 202a and second subject 202b.

The controller 106 may determine, based on the determined amount of exposure time for each of the subjects 202a, 202b, whether to cause the light source 104 to cease emitting the UV light. For example, if the predetermined amount of time is about six minutes and the controller 106 determines, based on the received detection data, that the first subject 202a has been exposed for three minutes and the second subject 202b has been exposed for less than one second, the controller 106 may not transmit a deactivation signal to the light source 104. As such, in FIG. 4B, the light source 104 at time $t_1$ continues to emit UV light.

Figure 4C:
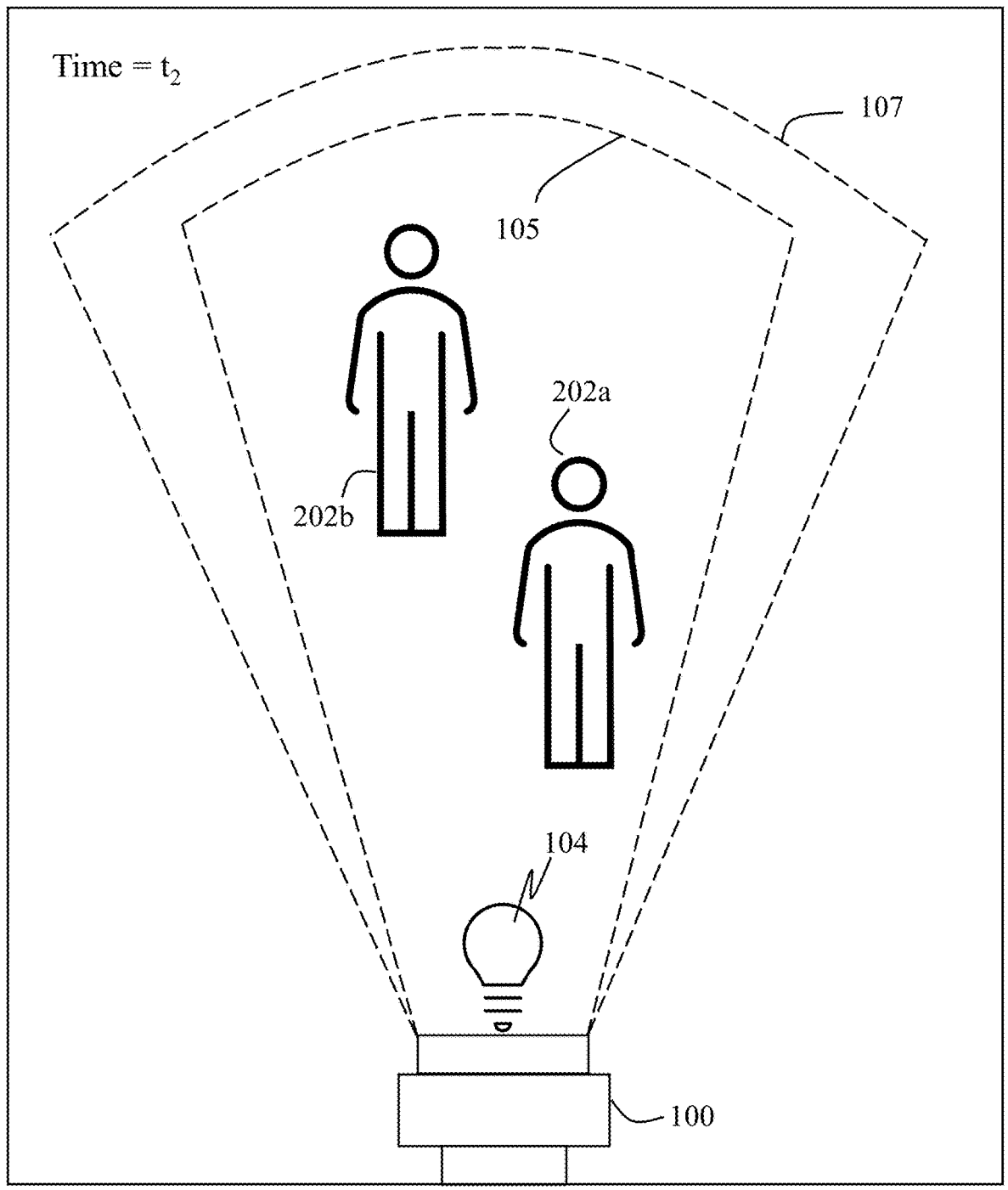

In FIG. 4C, at a time $t_2$ occurring after the time $t_1$ the first subject 202a and second subject 202b remain located within of the emission range 105. The one or more subject detection sensors 108 may generate and transmit detection data to the controller 106 at the predetermined detection interval between times $t_2$ and $t_1$. The controller 106 may determine, based on the received detection data between times $t_2$ and $t_1$, the amount of time that each of the first subject 202a and second subject 202b have been within the emission range 105. The determined amount of exposure time for the first subject 202a may be generally equal to $t_2-t_0$. The amount of exposure time for the second subject 202b, determined by the controller 106, may be generally equal to $t_2-t_1$ where $t_1$ is the time at which the second subject 202b was first determined to be within the emission range. If the exposure time for the first subject 202a is equal to the predetermined amount of exposure time, but the amount of exposure time for the second subject is less than the predetermined amount of exposure time the controller 106 may transmit a deactivation signal to the light source 104 thereby causing the light source 104 to cease emitting UV light.

Figure 4D:
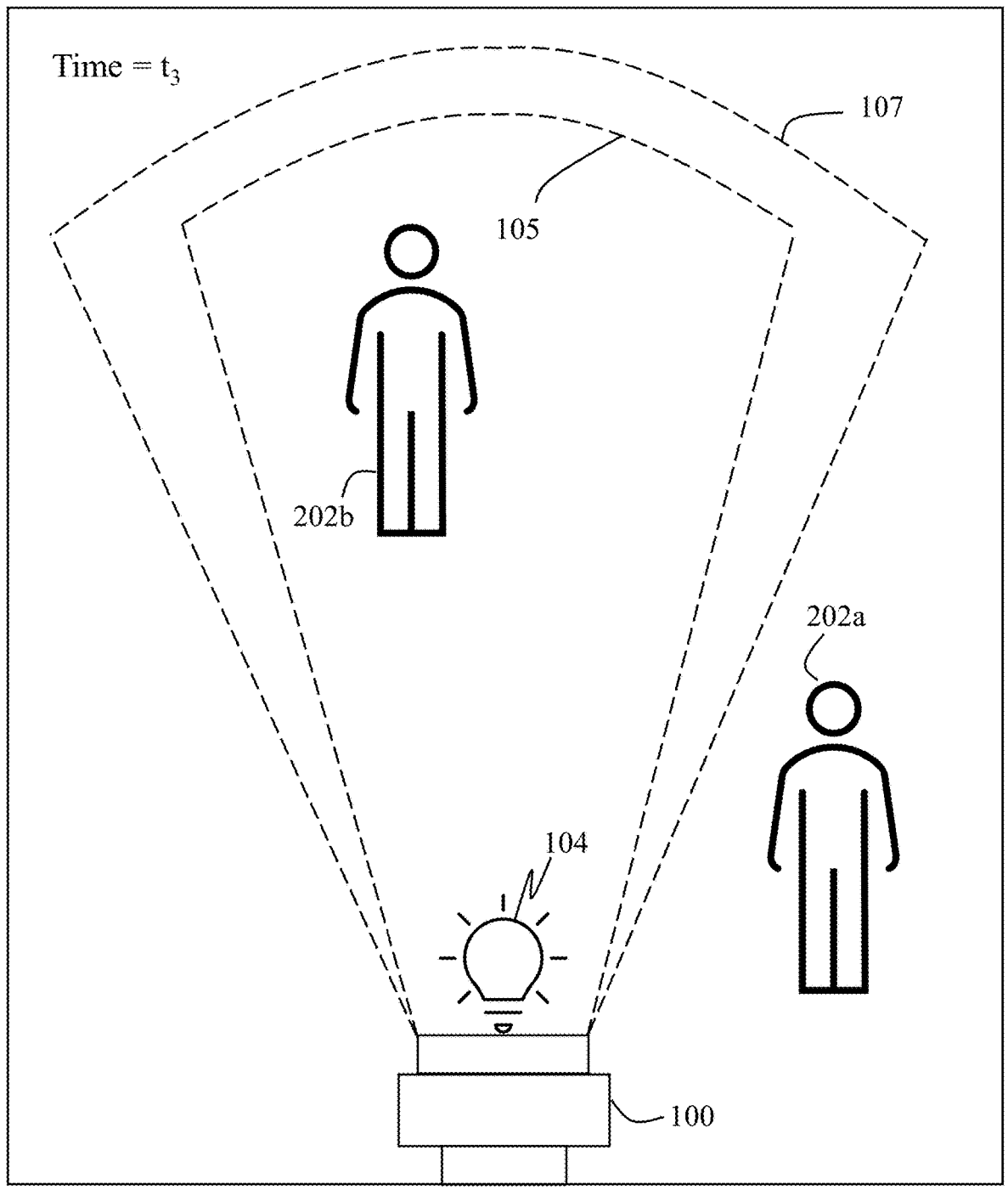

In FIG. 4D, at a time $t_3$ occurring after the time $t_2$, the first subject 202a has moved outside of the emission range 105. The subject detection sensors 108 may generate and transmit detection data to the controller at the predetermined detection interval between times $t_3$ and $t_2$. The controller 106 may determine, based on the received detection data, that at time $t_3$ the second subject 202b is within the emission range 105 and that the first subject 202a is not. The light source 104 between the times $t_3$ and $t_2$ was not active and as such was not emitting UV light. Therefore, between the times $t_3$ to $t_2$ neither of the first subject 202a and second subject 202b were exposed to UV light from the light source 104. As such, at time $t_3$ the controller 106 may determine the amount of exposure time for the second subject 202b. In this instance, the determined amount of exposure time for the second subject 202b is equal to $t_2-t_1$.

The controller 106 may determine whether the amount of exposure time for the second subject 202b is less than the predetermined amount of exposure time. For example, the amount of exposure time $t_2-t_1$ determined by the controller 106 for the second subject 202b may be three minutes and the predetermined amount of exposure time may be six minutes. As such, the controller 106, in this instance, may determine that the second subject 202b has not been exposed to UV light emitted by the light source 104 for the predetermined amount of time. The controller 106 may, in response to determining that the second subject 202b has not been exposed to the UV light for the predetermined amount of time, transmit an activation signal to the light source 104 to cause the light source 104 to emit UV light. In this manner, the UV device 100 may distinguish between different subjects in order to optimize an amount of time the UV device 100 may safely emit UV light to effect disinfection of the air and/or surfaces within the emission range 105.

In other embodiments, the controller 106 may be configured to activate and/or deactivate the light source 104 based on an aggregate amount of time one or more subjects have been exposed to the emitted UV light. For example, in FIG. 4D, the controller 106 determined that the second subject 202b was the only subject within the emission range 105 and that the second subject 202b had not been exposed to emitted UV light for the predetermined amount of exposure time and therefore causes the light source 104 to be activated. However, alternative to what is illustrated in FIG. 4D, in instances where the controller 106 is configured to control activation of the light source 104 based on an aggregation of determined subject exposure time, the controller 106 at time $t_3$ may not cause the light source 104 to activate. For example, the controller 106 at time $t_3$ may determine that the total amount of time that any subject 202a-202b has been within the emission range 105 is generally equal to $t_3-t_0$ which is greater than the predetermined amount of exposure time. As such, at time $t_3$ the controller 106 may not transmit an activation signal to the light source 104, because the light source 104 would have already been deactivated at time $t_2$ when the first subject 202a was exposed to the UV light for the predetermined amount of exposure time.

Figure 5A:
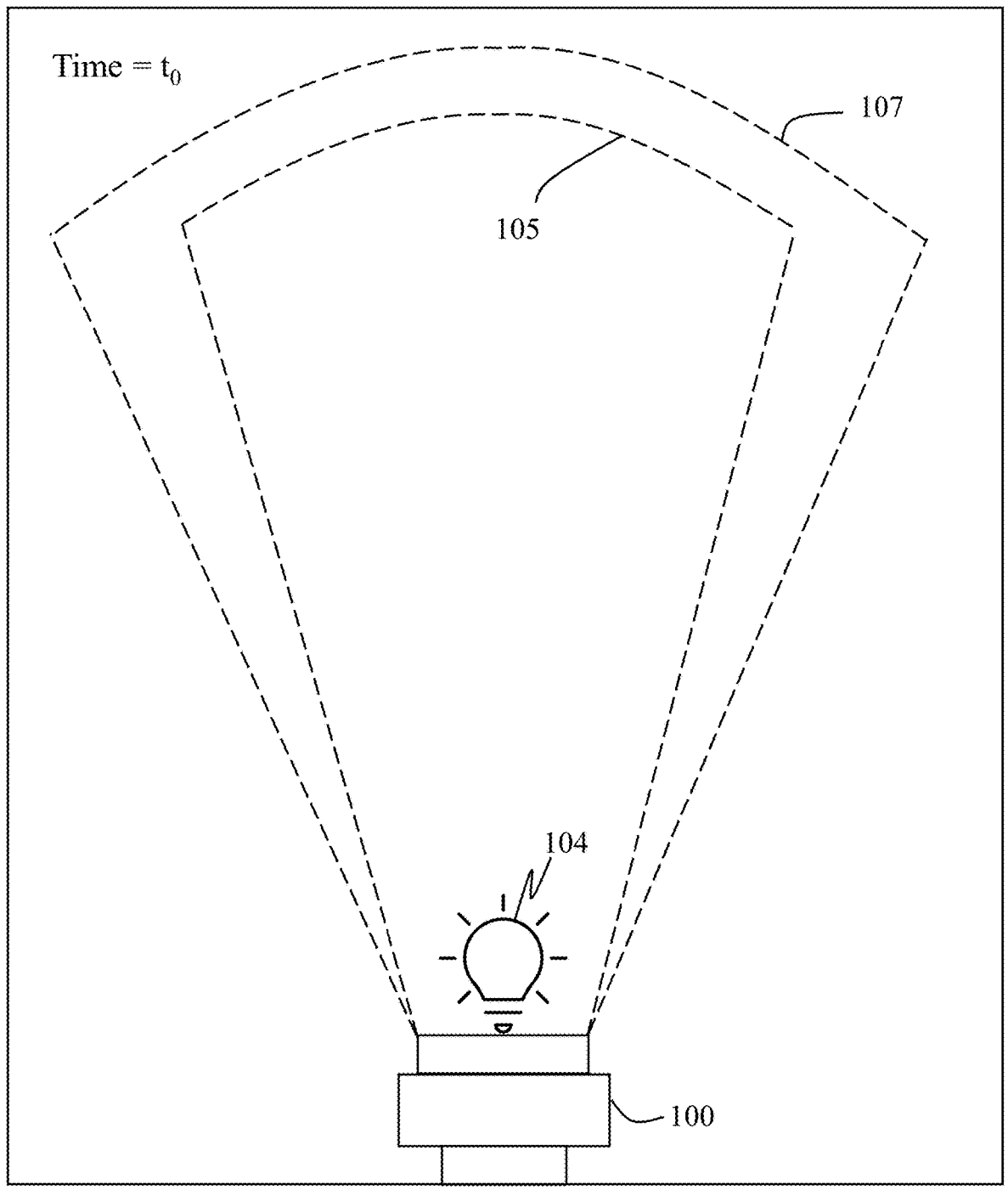
FIGS. 5A-5B are use case diagrams illustrating aspects of the present disclosure.
Figure 5B:
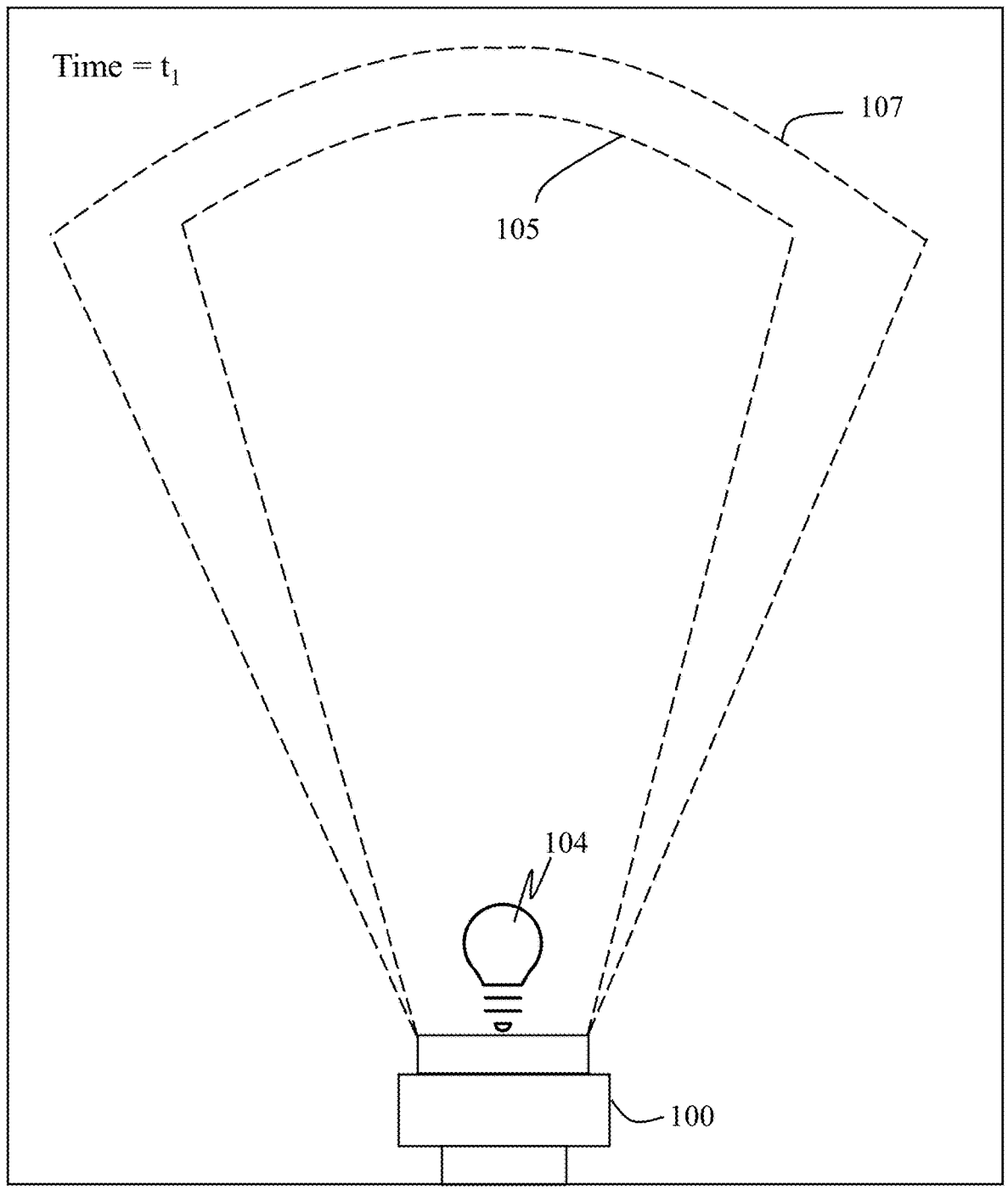

In some embodiments, the UV device 100 may be configured to cease emitting UV light in response to UV light being continuously emitted for a predetermined maximum period of time. Referring to FIGS. 5A-5B, there is illustrated a third use case in which the UV device emits UV light for up to a predetermined maximum period of time. In FIG. 5A at an initial time $t_0$ the light source 104 is activated and thereby is emitting UV light. The activation of the light source 104 may be in response to the controller 106 determining that no subjects are within the emission range 105 or that a subject within the emission range 105 has not remained therein for the predetermined amount of exposure time. For sake of brevity, it will be assumed in FIG. 5A that the controller 106 determines based on detection data generated by the subject detection sensors 108 at time $t_0$ that no subjects are within the emission range 105 and causes the light source 104 to emit UV light.

In FIG. 5B, at time $t_1$ occurring an amount of time after time $t_0$ the UV device 100 is still emitting UV light. The controller 106 may be configured to determine the amount of time that the light source 104 has been continuously emitting UV light. For example, the controller 106 may be in communication with the light source 104 such that the controller 106 may determine whether the light source 104 is active or not. In this manner, the controller 106 may determine that the light source 104 has been continuously emitting UV light for an amount of time equal to $t_1-t_0$. In response to the controller 106 determining at time $t_1$ that the amount of time $t_1-t_0$ is equal to a predetermined maximum emission amount of time, the controller 106 may cause the light source 104 to cease emitting UV light.

In some embodiments, the predetermined maximum emission amount of time may be less than or equal to the predetermined exposure limit for subjects exposed to the emitted UV light. In this manner, the UV device 100 may automatically cease to emit UV light prior to an exposure limit of a subject being reached. As such, the controller 106 being configured to deactivate the light source 104 at the predetermined maximum emission amount of time may act as an automatic safety measure to ensure no subject is exposed to UV light for a period of time great enough to cause adverse effects or damage thereto. In some embodiments, the predetermined maximum emission amount of time may be between about six minutes to about sixty minutes. In some embodiments, the predetermined maximum amount of time may be about ten minutes, about fifteen minutes, about twenty minutes, about twenty five minutes, about thirty minutes, about thirty five minutes, about forty minutes, about forty five minutes, about fifty minutes, about fifty five minutes, or about sixty minutes. In some embodiments, the predetermined maximum amount of time may be about two hours, three hours, four hours, five hours, six hours, seven hours, eight hours, nine hours, ten hours, eleven hours, twelve hours, thirteen hours, fourteen hours, fifteen hours, sixteen hours, seventeen hours, eighteen hours, nineteen hours, twenty hours, twenty-one hours, twenty-two hours, twenty-three hours, or twenty-four hours, within a twenty-four hour time cycle. In some embodiments, the predetermined maximum emission amount of time may be about fifteen minutes.

In some embodiments, the UV device 100 may be configured to calculate an effective disinfection rate based on an amount of time that the light source 104 has been emitting the UV light. For example, the controller 106 may monitor the amount of time which the light source 104 has been emitting UV light. The controller 106 may determine, based on the monitored amount of time, an effective disinfection rate representing the efficacy of disinfection of the air and/or surfaces within the range of the emitted UV light. In some embodiments, the controller 106 may transmit the determined effective disinfection rate to the client device 110. In this manner, a user of the client device 110 may be provided with a visual indication of the efficacy of the disinfection effected by the UV device 100.

Figure 6A:
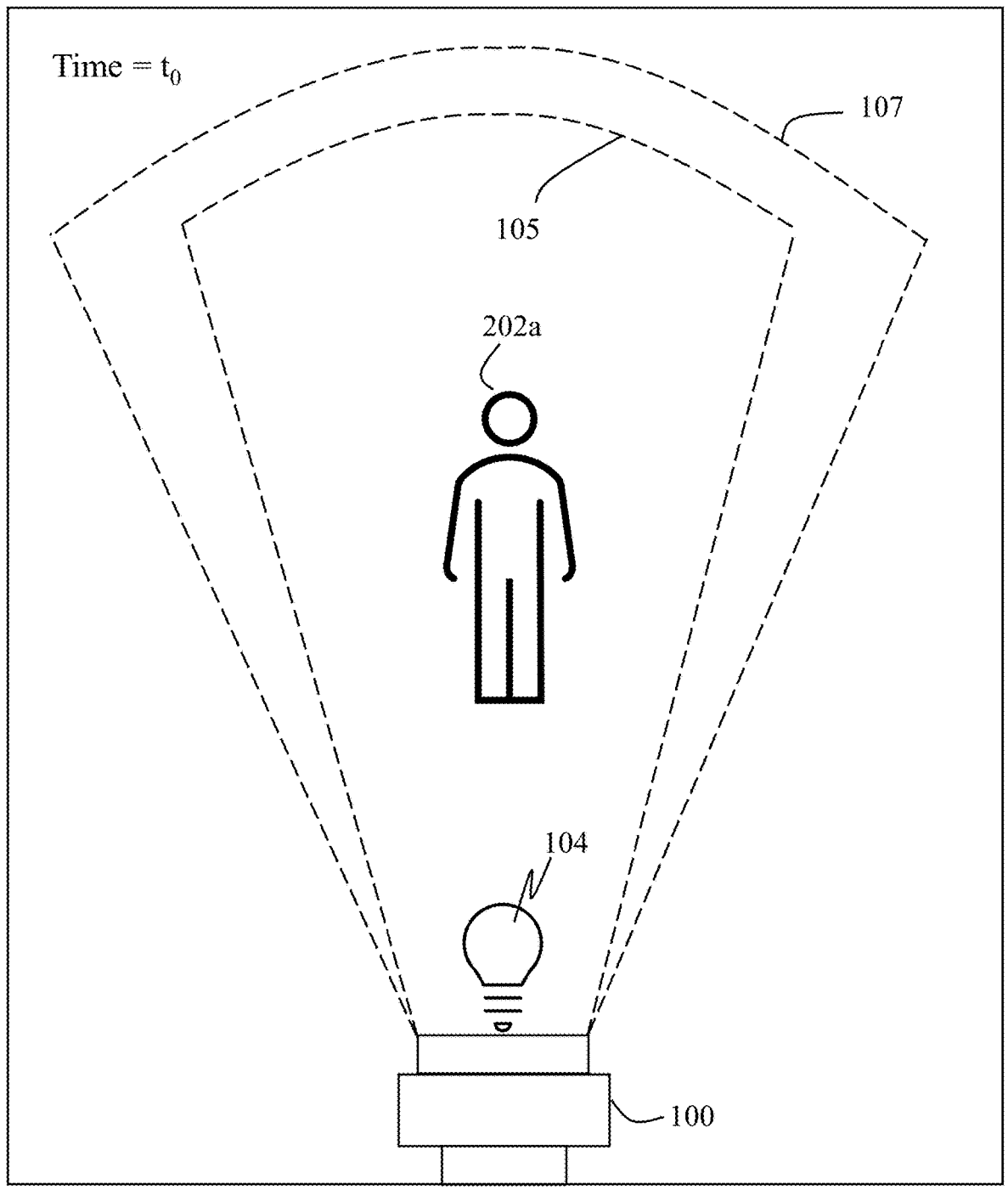
FIGS. 6A-6C are use case diagrams illustrating aspects of the present disclosure.
Figure 6B:
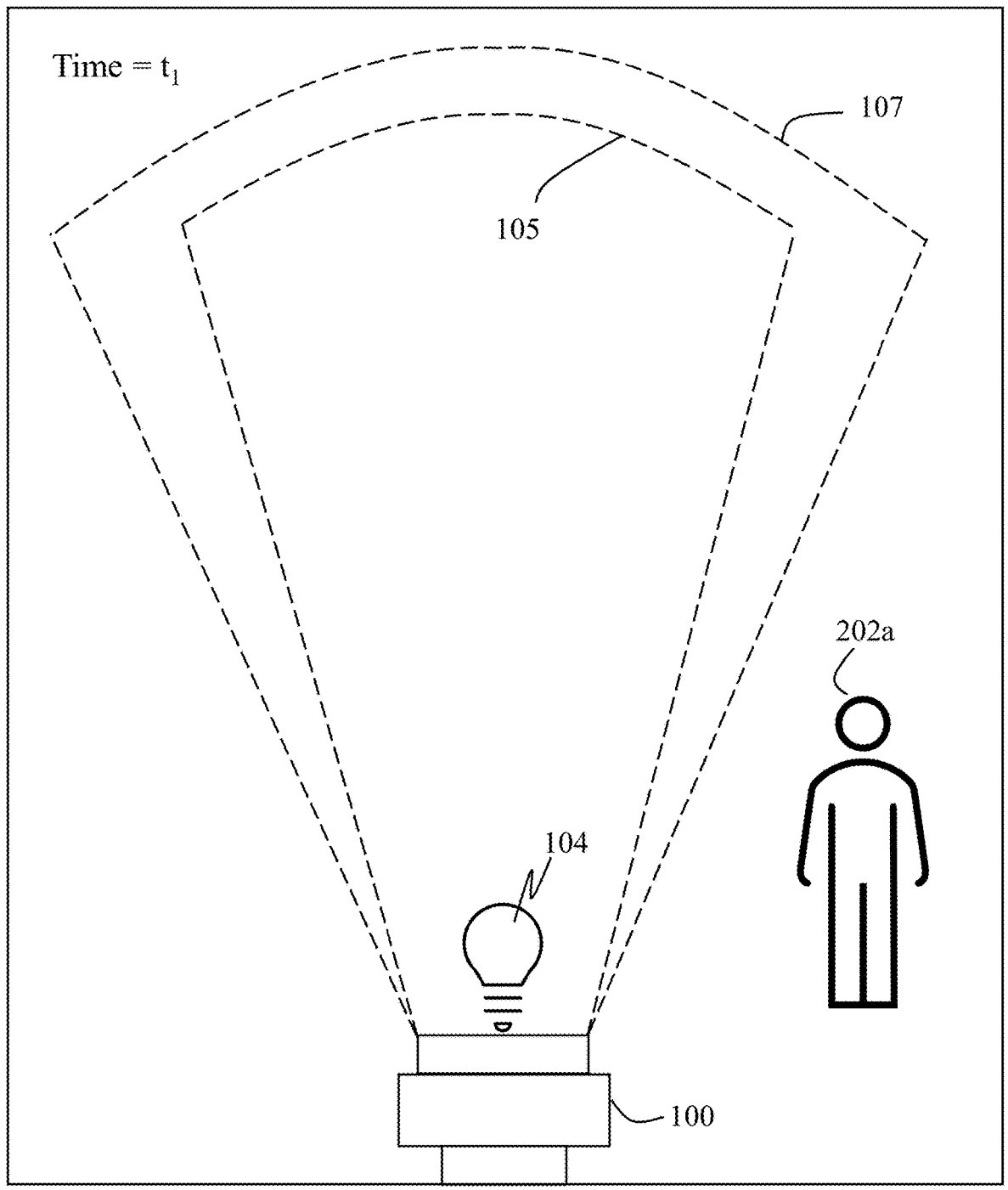
Figure 6C:
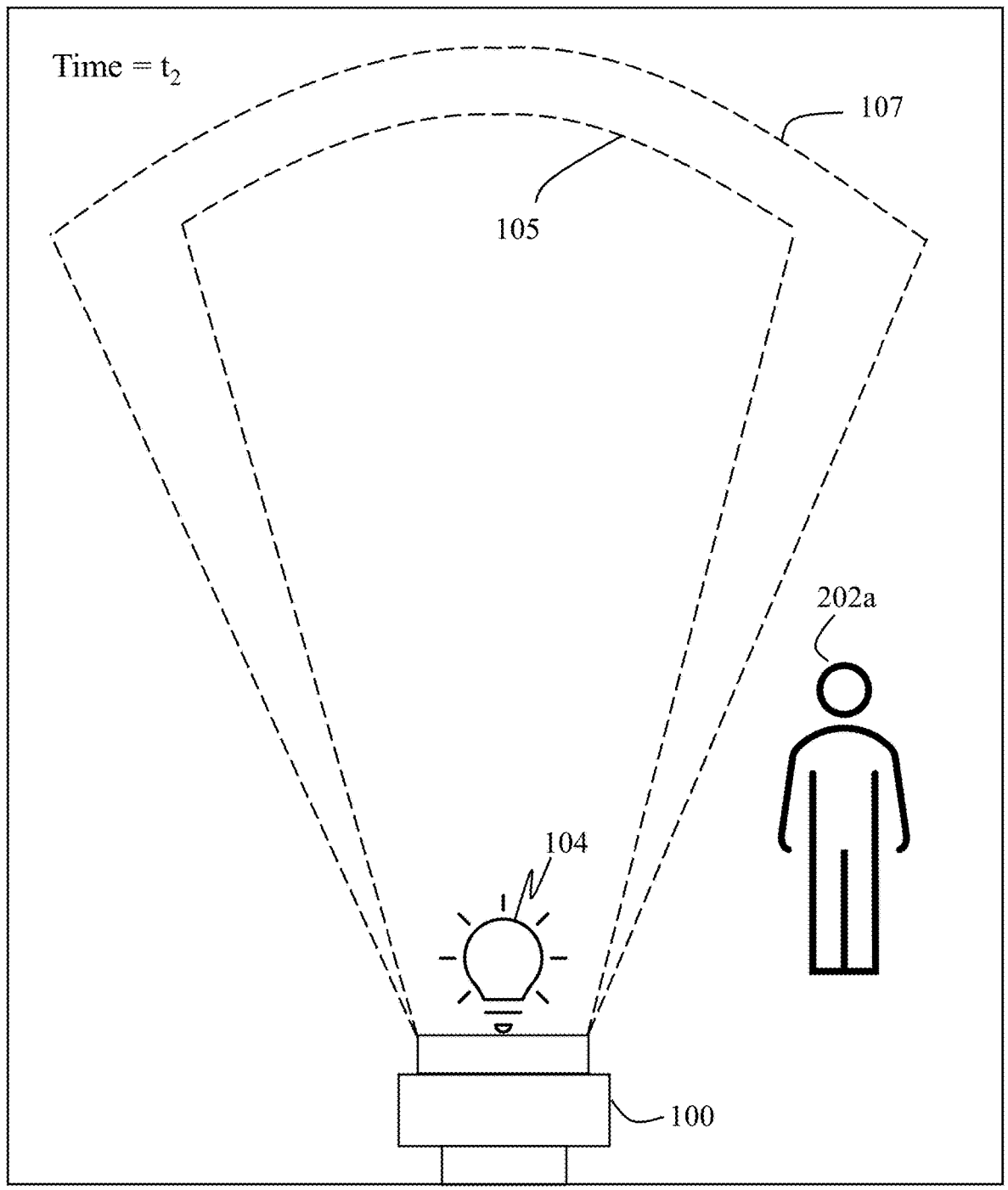

In some embodiments, the UV device 100 is configured to delay reactivation of the light source 104 by a predetermined amount of delay time. Referring to FIGS. 6A-6C, the light source 104 may be deactivated by the controller 106 in response to a subject being within range of the emitted UV light for the predetermined amount of exposure time (e.g., as discussed above with reference to FIGS. 3A-3C) or the UV light source emitting UV light for the predetermined maximum emission amount of time (e.g., as discussed above with reference to FIGS. 5A-5B). In FIG. 6A, the light source 104 is deactivated at time $t_0$ in response to the subject 202a being within the emission range 105 for the predetermined amount of exposure time. The controller 106 may be configured to begin tracking the amount of time that the light source 104 has not been active. For example, at time $t_0$ the controller 106 may begin recording the amount of time that the light source has not been active.

In FIG. 6B, at time $t_1$ occurring an amount of time after time $t_0$ the subject 202a has moved outside of the emission range 105. The controller 106 may determine that the subject 202a has moved outside of the emission range 105 and determine whether the amount of time between times $t_1$ and $t_0$ is greater than or equal to the predetermined amount of delay time. In FIG. 6B, the controller 106 determines that the amount of time $t_1-t_0$ is not greater than or equal to the predetermined amount of delay time and therefore does not cause the light source 104 to emit UV light. As such, the light source 104 has not been active between times $t_1$ and $t_0$.

In FIG. 6C, at time $t_2$ occurring an amount of time after time $t_1$ the subject 202a has remained outside of the emission range 105. The controller 106 may determine that no subject is within the emission range 105 and may determine whether the amount of time lapsed between times $t_2$ and $t_0$ are greater than or equal to the predetermined amount of delay time. In response to the controller 106 determining that the amount of time $t_2-t_0$ is greater than or equal to the predetermined amount of delay time, the controller 106 may cause the light source 104 to emit UV light. In some embodiments, the controller 106 is configured to cause the light source 104 to emit UV light in response to the light source 104 being deactivated for the predetermined amount of delay time regardless of whether a subject is within the emission range 105. In other embodiments, the controller 106 may be configured to only activate the light source 104 in response to determining that no subject is within the emission range and that the predetermined amount of delay time has been reached. In some embodiments, the predetermined amount of delay time is between about one second to fifteen minutes. In some embodiments, the predetermined amount of delay time is about six minutes.

In some embodiments, the UV device 100 may be configured to emit UV light based on one or more user inputs transmitted from the client device 110 to the UV device 100. For example, a user may, at the client device 110 input one or more desired activation times corresponding to one or more periods of time the user wishes the UV device 100 to emit UV disinfecting light. Put another way, the user may, at the client device 110 input a desired schedule with which the user wishes the UV device to operate within. In some embodiments, the UV device 100 is configured prioritize safety operations (e.g., emission and ceasing emission of UV light based on the safety operations described above, for example, with reference to FIGS. 3A-6C) over the user input desired schedule. As such, the schedule input by the user may include an indication of one or more start times and stop times corresponding to when the UV device 100 should be emitting UV light and when the UV device 100 should not.

Referring to FIGS. 7A-7D, there is shown a use case illustrating the UV device 100 operating within a desired continuous activation period input by a user at the client device 110. Prior to what is illustrated in FIGS. 7A-7D, the user may input, at the client device 110, an indication of a desired continuous activation period, or, put another way an indication of a continuous period of time within which the user wishes for the UV device 100 to emit UV light. The indication of a desired continuous activation period may be defined by a start time and a stop time. For example, the desired continuous activation period may be defined by a start time of 10:00 AM and a stop time of 4:00 PM. In this manner, the UV device 100 may enable a user to remotely control operation of the UV device 100. This may be beneficial such that the user may define different operating times of the UV device 100 corresponding to times in which the user may be away from the UV device (e.g., when the user is at work, school, or generally out of their home or a room in which the UV device 100 is located). The indication of the continuous activation period may be transmitted from the client device 110 to the controller 106.

Figure 7A:
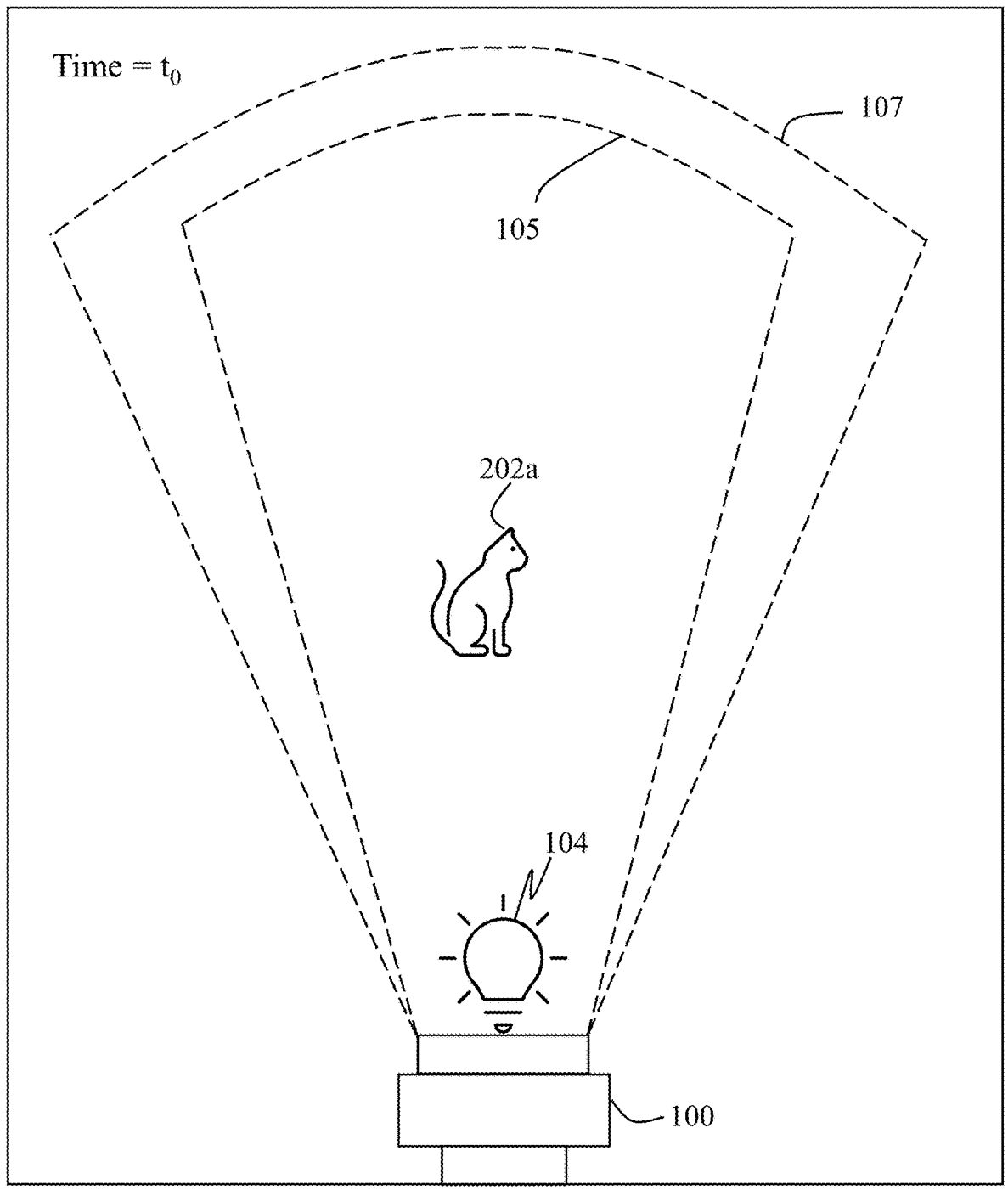
FIGS. 7A-7D are use case diagrams illustrating aspects of the present disclosure.

In FIG. 7A, at time $t_0$ the controller 106 determines that the time $t_0$ corresponds to the start time of the desired continuous activation period. As such, at time $t_0$ the controller 106 may transmit the activation signal to the light source 104 to cause the light source 104 to emit UV light. In some embodiments, the controller 106 may be configured to activate the light source 104 in response to the current time (e.g., time $t_0$) being the same as the desired start time and in response to determining that a subject within the emission range 105 has not been exposed to UV light within the emission range 105 for the predetermined amount of exposure time.

For example, in FIG. 7A, a subject 202a (e.g., a domesticated animal) is within the emission range 105. The controller 106 may have, prior to the time $t_0$ been receiving detection data from the subject detection sensors and determined that the subject 202a was within the emission range 105. In one instance the light source 104 may be active prior to time $t_0$ and the subject 202a may be within the emission range 105 for a period of time less than the predetermined amount of exposure time. As such, in response to the time $t_0$ coinciding with the start time, the controller 106 may transmit the activation signal to the light source 104 at time $t_0$. In another instance, the light source 104 may have been active prior to time $t_0$ and the subject 202a may have been within the emission range 105 for a period of time equal to the predetermined amount of exposure time. As such, at time prior to time $t_0$ the controller 106 may cause the light source 104 to cease emitting UV light. Furthermore, in an instance where the subject 202a remains within the emission range 105 at time $t_0$ the controller 106 may not cause the light source 104 to emit UV light even though the time $t_0$ coincides with the user input start time.

Figure 7B:
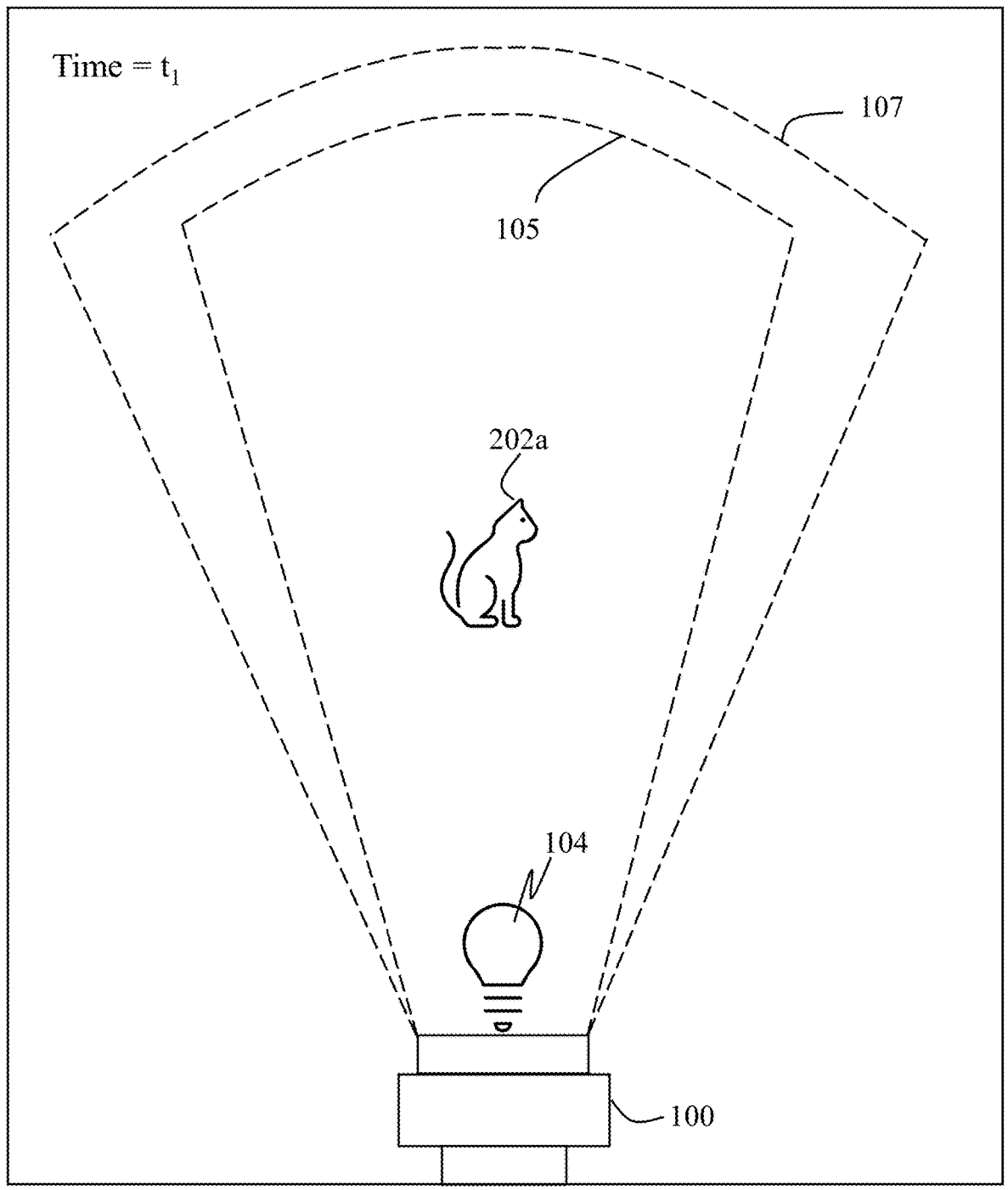

For sake of brevity though, it will be assumed at time $t_0$ in FIG. 7A that the light source 104 is activated. In FIG. 7B, at a first time $t_1$ following the start time $t_0$ and prior to the user specified end time, the controller 106 may determine that one or more subjects are within the emission range 105 of the activated light source 104. In some embodiments, in response to the controller 106 determining that a subject (e.g., subject 202a) being within the emission range 105 at time $t_1$ the controller 106 may transmit a deactivation signal to the light source 104 to cause the light source 1094 to cease emitting UV light. In other embodiments, the controller 106 may determine, based on detection data received at the predetermined detection interval between times $t_0$ and $t_1$ that the subject 202a has remained within the emission range 105 for the predetermined amount of exposure time. As such, the controller 106 at time $t_1$ may transmit the deactivation signal to the light source 104.

Figure 7C:
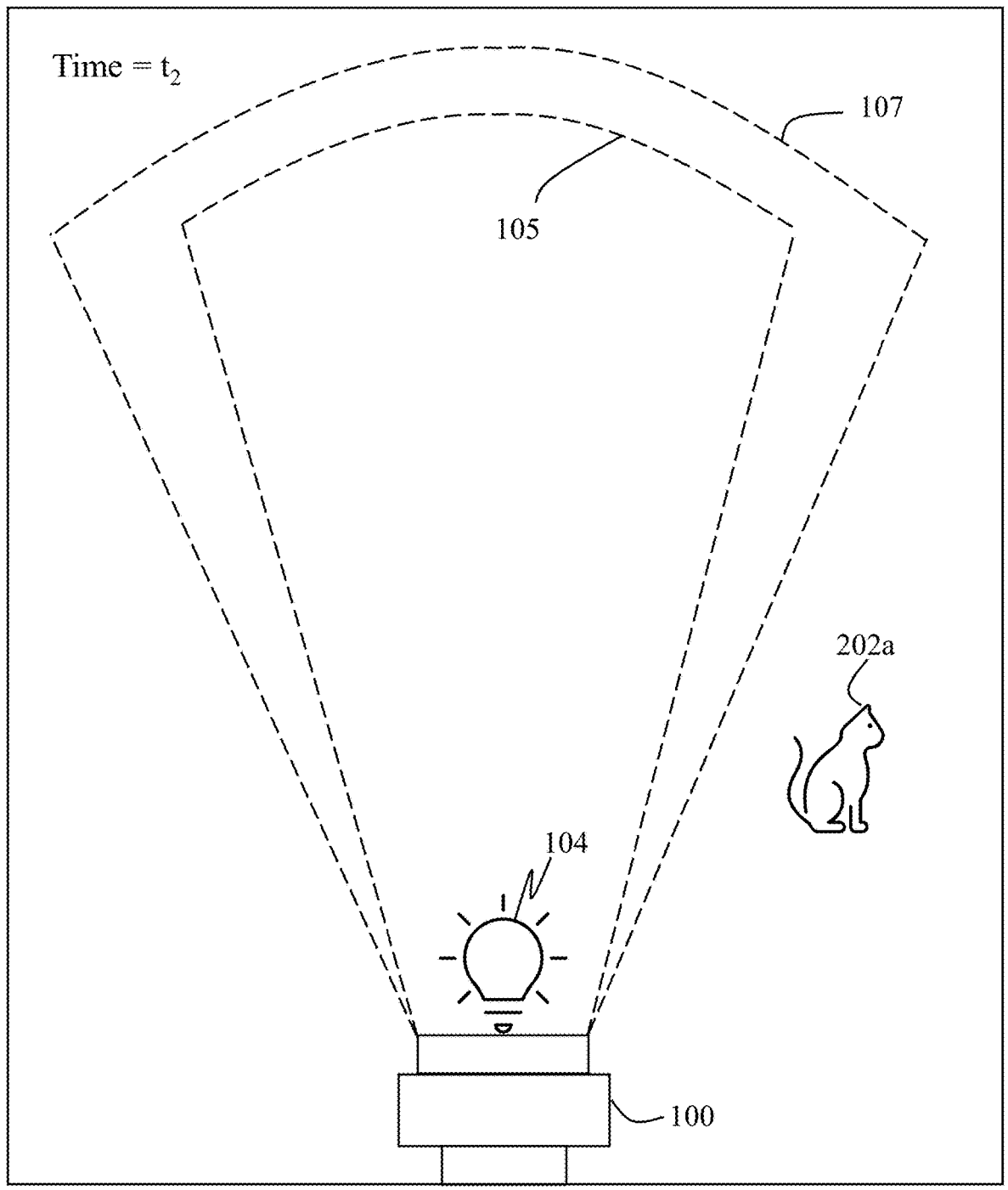

In FIG. 7C, at a second time $t_2$ following the first time $t_1$ and prior to the user specified stop time, the controller 106 may determine that no subject is within the emission range 105 of the light source 104 and may cause the light source 104 to emit UV light. For example, in FIG. 7C, at time $t_2$ the subject 202a has moved outside of the emission range 105. The controller 106 determines, based on received detection data received from the subject detection sensors 108 at time $t_2$ that no subject is within the emission range 105. In response to determining that no subject is within the emission range 105 and that the time $t_2$ falls within the desired continuous activation period, the controller 106 transmits the activation signal to the light source 104 to cause the light source 104 to emit UV light.

Figure 7D:
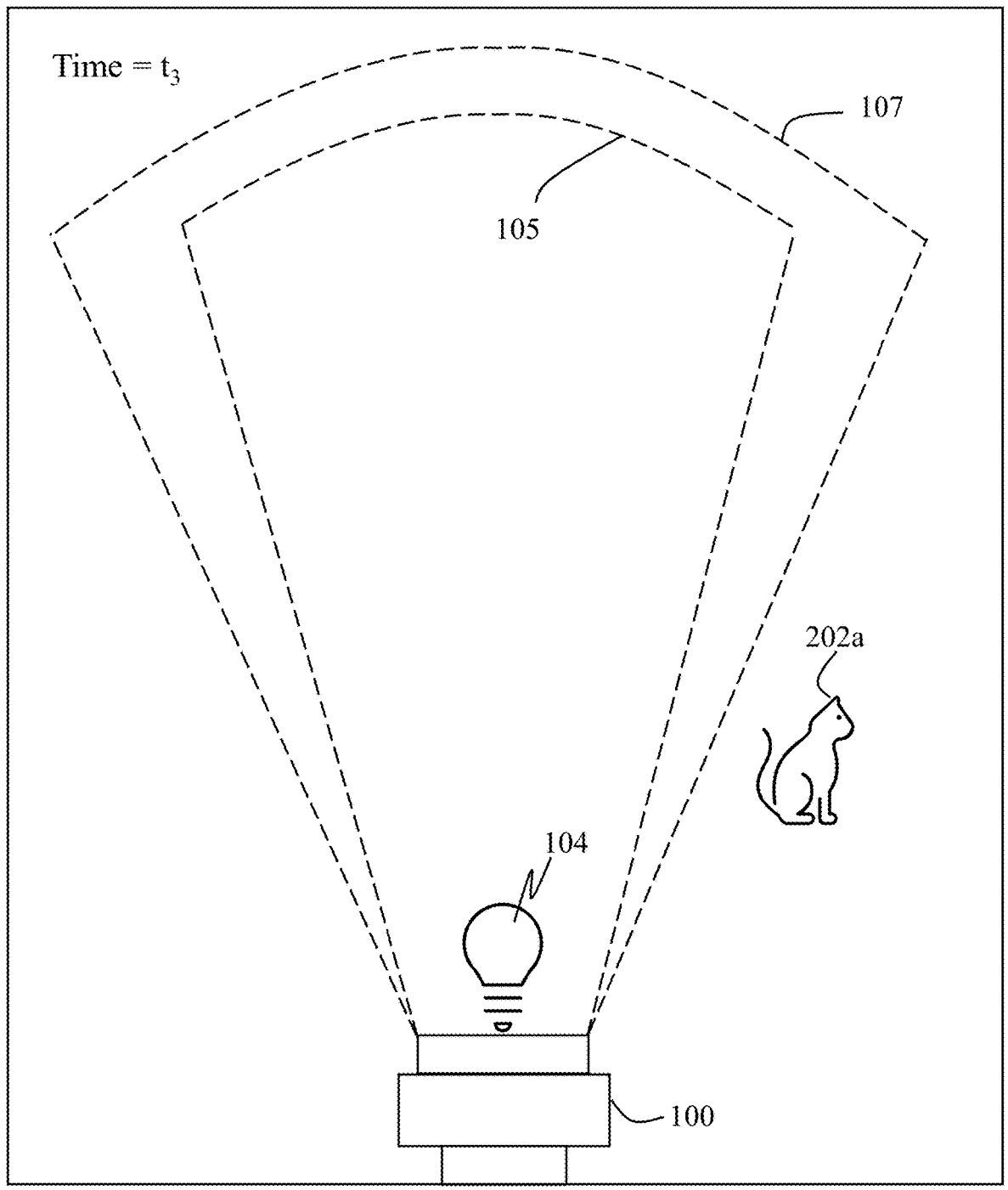

In FIG. 7D, at a third time $t_3$, the controller 106 may determine that the third time $t_3$ coincides with, or is equal to, the user specified end time. In response to determining that the third time $t_3$ is equal to the user specified end time, the controller 106 may transmit a deactivation signal to the light source 104 to cause the light source 104 to cease emitting UV light. In some embodiments, in response to determining that the third time $t_3$ is equal to the end time, the controller 106 may cause the light source 104 to cease emitting UV light regardless of whether a subject is within the emission range 105 or not. For example, in FIG. 7D, there are no subjects within the emission range 105, however, the controller 106 determines that the user specified end time has been reached and therefore causes the light source 104 to cease emitting UV light.

In some embodiments, the UV device 100 may be configured to perform redundant detection for subjects within the emission range of the light source 104 to improve the safety of the UV device 100. For example, aspects of the present disclosure are discussed above in FIGS. 3A-7D with reference to the generation of detection data by one or more subject detection sensors 108 and determining, at the controller 106, a position of one or more subjects relative to the emission range 105. In this manner, the controller 106, or a processor included therein, and one or more of the subject detection sensors 108 may act as a first safeguard system for ensuring that subjects are not exposed to UV light emitted by the light source 104 for an amount of time that would cause adverse effects and/or damage. As such, the UV device 100 may include a second safeguard system, which may include additional subject detection sensors (not shown) and/or a subset of the subject detection sensors 108 illustrated in FIGS. 1-2. Furthermore, the second safeguard system may include a second processor and/or second controller generally the same as controller 106 or a processor included therewith. The second safeguard system may be configured to operate in generally the same manner as, and independently of, the first safeguard system and as such will not be discussed in extensive detail for sake of brevity. However, it should be understood that the UV device 100 may be configured to leverage both the first and second safeguard systems simultaneously to automatically activate or deactivate the light source 104 as described above.

It will be appreciated by those skilled in the art that changes could be made to the exemplary embodiments shown and described above without departing from the broad inventive concepts thereof. It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways.

Specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one". Finally, unless specifically set forth herein, a disclosed or claimed method should not be limited to the performance of their steps in the order written, and one skilled in the art can readily appreciate that the steps may be performed in any practical order. When specifying a numerical value or range of values, the term "about" means +/−10% unless otherwise defined.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

What is claimed is:

1. A far-ultraviolet (far-UVC) disinfection device comprising:
   a housing;
   a light source positioned within the housing and configured to emit a far-UVC light having an output wavelength of between about 206 nanometers to about 230 nanometers;
   one or more subject detection sensors positioned within the housing and configured to detect the presence of one or more subjects, the one or more subjects consisting of one or more of human beings, one or more domesticated animals, and one or more farm animals or a combination thereof; and
   a controller positioned within the housing and in communication with the light source and the one or more subject detection sensors, the controller configured to:
      receive detection data from the one or more subject detection sensors;
      determine, based on the received detection data, whether one or more subjects are within a range of the far-UVC light emitted by the light source;
   in response to determining that the one or more subject detection sensors detect the presence of the one or more subjects within the range of the far-UVC light emitted by the light source for a predetermined amount of exposure time, cause the light source to cease emitting the far-UVC light;
   in response to determining that no subject of the one or more subjects is within the range of the far-UVC light emitted by the light source for the predetermined amount of exposure time, cause the light source to emit the far-UVC light; and
   determine an effective disinfection rate based on an amount of time that the light source has been emitting the far-UVC light.

2. The far-UVC disinfection device of claim 1, wherein the one or more subject detection sensors includes at least one of an infrared sensor, a motion sensor, and a proximity sensor.

3. The far-UVC disinfection device of claim 1, wherein the predetermined amount of exposure time is less than or equal to an exposure limit for the one or more subjects being exposed to the far-UVC light emitted by the light source.

4. The far-UVC disinfection device of claim 1, wherein in response to the one or more subject detection sensors detecting the presence of one or more subjects within range of the emitted far-UVC light for between about one minute to about ten minutes, the controller is configured to cause the light source to cease emitting the far-UVC light.

5. The far-UVC disinfection device of claim 1, wherein in response to the one or more subject detection sensors detecting the presence of one or more subjects within the range of the emitted far-UVC light for about six minutes, the controller is configured to cause the light source to cease emitting the far-UVC light.

6. The far-UVC disinfection device of claim 1, wherein the controller is configured to transmit the determined effective disinfection rate to at least one of: a smart phone, a tablet computer, a laptop computer, and a desktop computer, each of which being external to the far-UVC disinfection device.

7. The far-UVC disinfection device of claim 1, wherein the one or more subject detection sensors includes two infrared sensors and four motion sensors.

8. The far-UVC disinfection device of claim 1, wherein the controller is configured to cause the one or more subject detection sensors to generate the detection data and transmit the detection data to the controller at a predetermined detection interval.

9. The far-UVC disinfection device of claim 8, wherein the predetermined detection interval is less than or equal to one second.

10. The far-UVC disinfection device of claim 1, wherein the controller is configured to delay causing the light source to emit the far-UVC light in response to the one or more subject detection sensors detecting no subject within the range of the far-UVC light emitted by the light source by a predetermined amount of delay time.

11. The far-UVC disinfection device of claim 10, wherein the predetermined amount of delay time is between about one second to six minutes.

12. The far-UVC disinfection device of claim 1, wherein the controller is further configured to:
   in response to the light source emitting the far-UVC light continuously for a predetermined maximum emission amount of time, causing the light source to cease emitting the far-UVC light.

13. The far-UVC disinfection device of claim 12, wherein the predetermined maximum emission amount of time is about sixty minutes.

14. The far-UVC disinfection device of claim 1, wherein the light source is configured to emit a far-UVC light having an output wavelength of about 222 nanometers.

15. The far-UVC disinfection device of claim 1, wherein the controller is configured to cause the light source to cease emitting the far-UVC light in response to the one or more subject detection sensors detecting the presence of a subject within the range of the emitted far-UVC light for a threshold limit value (TLV) amount of time, wherein the TLV amount of time is based on the output wavelength of the emitted far-UVC light.

16. The far-UVC disinfection device of claim 1, wherein the controller is configured to cause the light source to cease emitting the far-UVC light in response to the one or more subject detection sensors detecting the presence of a subject within a predetermined distance of the light source.

17. The far-UVC disinfection device of claim 16, wherein the predetermined distance is about three feet.

18. A far-ultraviolet (far-UVC) disinfection device comprising:
   a housing;
   a light source positioned within the housing and configured to emit a far-UVC light having an output wavelength of between about 206 nanometers to about 230 nanometers;
   one or more subject detection sensors positioned within the housing and configured to detect the presence of one or more subjects, the one or more subjects consisting of one or more of human beings, one or more domesticated animals, and one or more farm animals or a combination thereof; and
   a controller positioned within the housing and in communication with the light source and the one or more subject detection sensors, the controller configured to:

receive detection data from the one or more subject detection sensors;

determine, based on the received detection data, whether one or more subjects are within a range of the far-UVC light emitted by the light source;

in response to determining that the one or more subject detection sensors detect the presence of the one or more subjects within the range of the far-UVC light emitted by the light source for between about one minute to about ten minutes, cause the light source to cease emitting the far-UVC light; and in response to determining that no subject of the one or more subjects is within the range of the far-UVC light emitted by the light source for about one minute to about ten minutes, cause the light source to emit the far-UVC light.

19. A far-ultraviolet (far-UVC) disinfection device comprising:

a housing;

a light source positioned within the housing and configured to emit a far-UVC light having an output wavelength of between about 206 nanometers to about 230 nanometers;

one or more subject detection sensors positioned within the housing and configured to detect the presence of one or more subjects, the one or more subjects consisting of one or more of human beings, one or more domesticated animals, and one or more farm animals or a combination thereof; and a controller positioned within the housing and in communication with the light source and the one or more subject detection sensors, the controller configured to:

receive detection data from the one or more subject detection sensors;

determine, based on the received detection data, whether one or more subjects are within a range of the far-UVC light emitted by the light source;

in response to determining that the one or more subject detection sensors detect the presence of the one or more subjects within the range of the far-UVC light emitted by the light source for about six minutes, cause the light source to cease emitting the far-UVC light; and in response to determining that no subject of the one or more subjects is within the range of the far-UVC light emitted by the light source for about six minutes, cause the light source to emit the far-UVC light.

* * * * *